(12) United States Patent
Kalatzis et al.

(10) Patent No.: US 11,072,803 B2
(45) Date of Patent: Jul. 27, 2021

(54) HYBRID DUAL RECOMBINANT AAV VECTOR SYSTEMS FOR GENE THERAPY

(71) Applicants: INSERM (INSTITUT NATIONAL DE LA SANTE ET DE LA RECHERCHE MEDICALE), Paris (FR); UNIVERSITE DE NANTES, Nantes (FR); CENTRE HOSPITALIER UNIVERSITAIRE DE NANTES, Nantes (FR); UNIVERSITÉ DE MONTPELLIER, Montpellier (FR)

(72) Inventors: Vasiliki Kalatzis, Montpellier (FR); Achille Francois, Nantes (FR)

(73) Assignees: INSERM (INSTITUT NATIONAL DE LA SANTE ET DE LA RECHERCHE MEDICALE), Paris (FR); UNIVERSITÉ DE NANTES, Nantes (FR); CENTRE HOSPITALIER UNIVERSITAIRE DE NANTES, Nantes (FR); UNIVERSITÉ DE MONTPELLIER, Montpellier (FR)

( * ) Notice: Subject to any disclaimer, the term of this patent is extended or adjusted under 35 U.S.C. 154(b) by 363 days.

(21) Appl. No.: 16/065,145

(22) PCT Filed: Dec. 21, 2016

(86) PCT No.: PCT/EP2016/082149
§ 371 (c)(1),
(2) Date: Jun. 22, 2018

(87) PCT Pub. No.: WO2016/108931
PCT Pub. Date: Dec. 21, 2016

(65) Prior Publication Data
US 2019/0002916 A1   Jan. 3, 2019

(30) Foreign Application Priority Data
Dec. 22, 2015   (EP) .................................. 15307104

(51) Int. Cl.
*C12N 15/86*   (2006.01)
*A61K 48/00*   (2006.01)
*A61P 27/02*   (2006.01)

(52) U.S. Cl.
CPC ............ *C12N 15/86* (2013.01); *A61K 48/005* (2013.01); *A61P 27/02* (2018.01); *C12N 2750/14143* (2013.01); *C12N 2750/14171* (2013.01); *C12N 2800/40* (2013.01); *C12N 2840/20* (2013.01); *C12N 2840/445* (2013.01)

(58) Field of Classification Search
CPC ......... A61K 48/005; A61P 27/02; C12N 5/86; C12N 2750/14143; C12N 2840/44; C12N 2840/445
USPC ..................... 435/6.1, 91.1, 91.31, 455, 458; 514/44 R, 44 A; 536/23.1, 24.5
See application file for complete search history.

(56) References Cited

U.S. PATENT DOCUMENTS

2010/0003218 A1   1/2010   Duan et al.
2016/0076054 A1*  3/2016   Auricchio ............ A61K 48/005
                                                      424/93.2

FOREIGN PATENT DOCUMENTS

| WO | WO 99/15684    | 4/1999  |
| WO | WO 2014/170480 | 10/2014 |
| WO | WO 2015/162302 | 10/2015 |
| WO | WO 2016/139321 | 9/2016  |

OTHER PUBLICATIONS

Trapani, I. et al. "Improved dual AAV vectors with reduced expression of truncated proteins are safe and effective in the retina of a mouse model of Stargardt disease" *Human Molecular Genetics*, 2015, pp. 6811-6825, vol. 24, No. 23.
Written Opinion in International Application No. PCT/EP2016/082149, dated Mar. 10, 2017, pp. 1-7.

* cited by examiner

*Primary Examiner* — Jane J Zara
(74) *Attorney, Agent, or Firm* — Saliwanchik, Lloyd & Eisenschenk

(57) ABSTRACT

The invention relates to constructs, vectors, relative host cells and pharmaceutical compositions which allow an effective gene therapy, in particular of genes larger than 5 Kb by using an improved hybrid dual recombinant AAV vector system.

Figure 1:
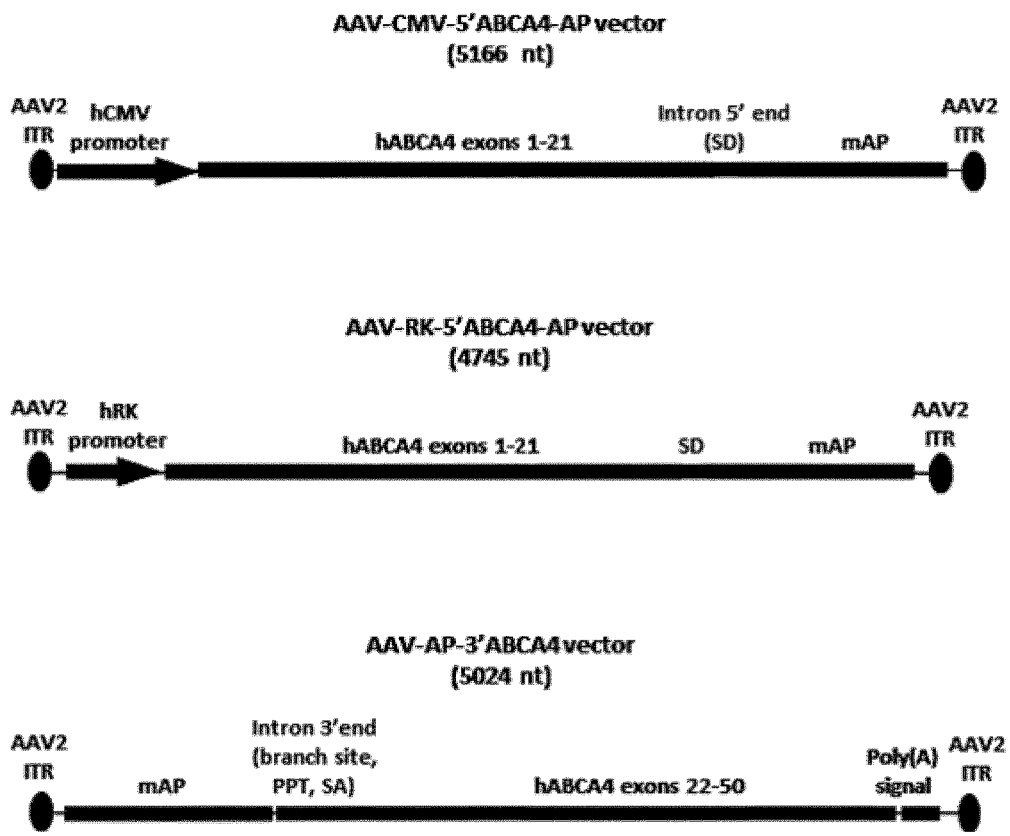

20 Claims, 8 Drawing Sheets
Specification includes a Sequence Listing.

A.

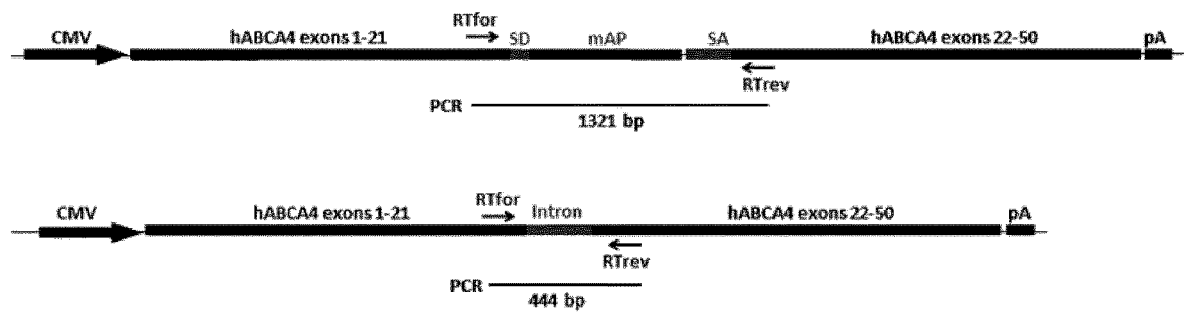

B.

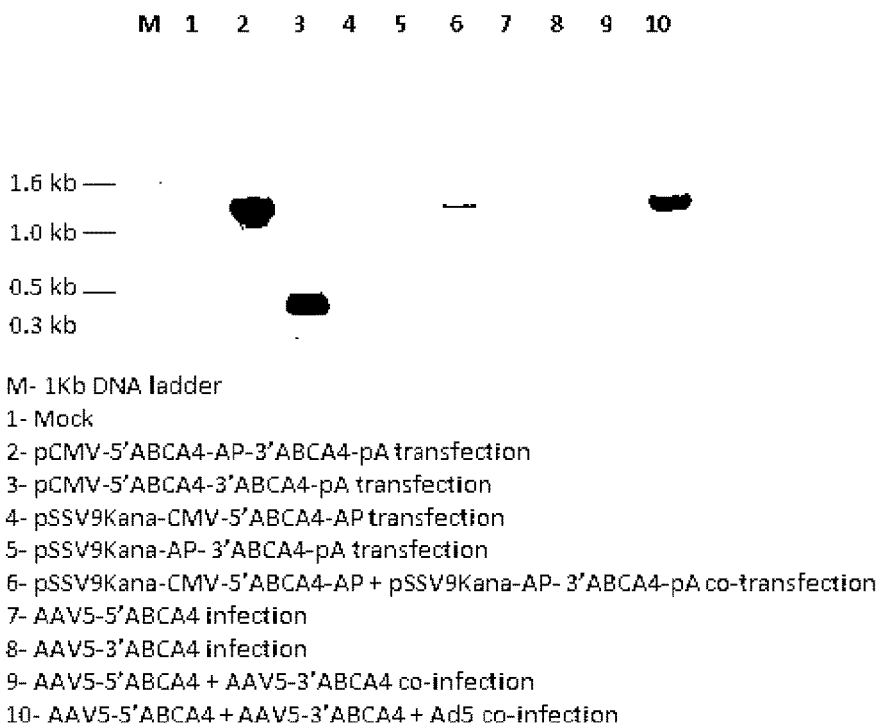

M- 1Kb DNA ladder
1- Mock
2- pCMV-5'ABCA4-AP-3'ABCA4-pA transfection
3- pCMV-5'ABCA4-3'ABCA4-pA transfection
4- pSSV9Kana-CMV-5'ABCA4-AP transfection
5- pSSV9Kana-AP- 3'ABCA4-pA transfection
6- pSSV9Kana-CMV-5'ABCA4-AP + pSSV9Kana-AP- 3'ABCA4-pA co-transfection
7- AAV5-5'ABCA4 infection
8- AAV5-3'ABCA4 infection
9- AAV5-5'ABCA4 + AAV5-3'ABCA4 co-infection
10- AAV5-5'ABCA4 + AAV5-3'ABCA4 + Ad5 co-infection Notes:
4, 5, 6: Plasmids were linearized prior to transfection
7, 8, 9, 10: AAV5 MOI was $10^5$ vg/cell
10: Ad5 MOI was 10 ip/cell

Figure 3

A.
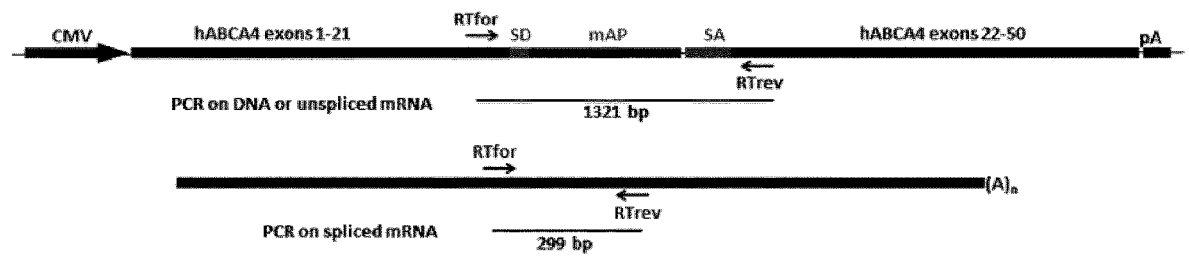
B.
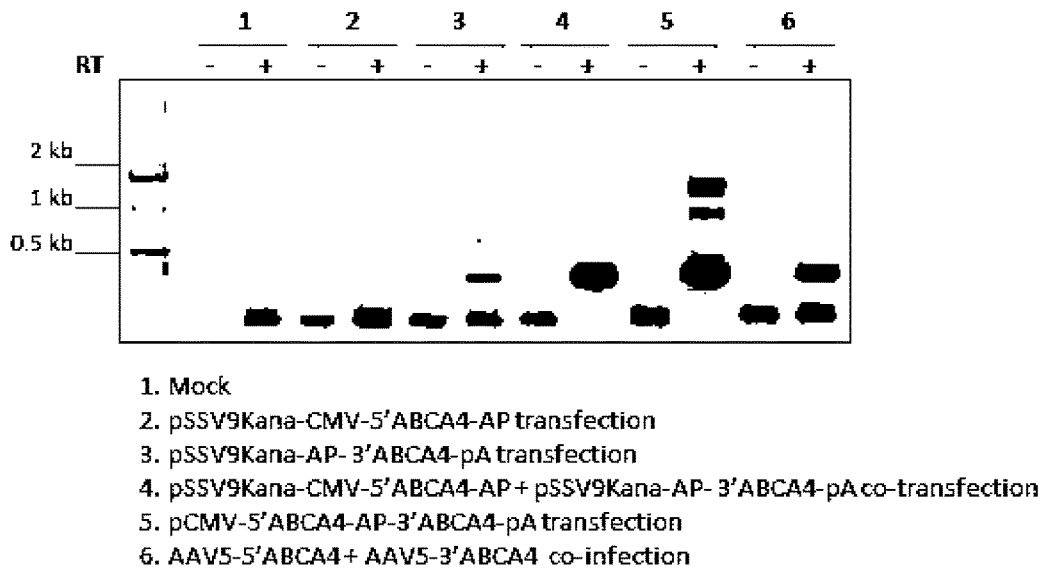
1. Mock
2. pSSV9Kana-CMV-5'ABCA4-AP transfection
3. pSSV9Kana-AP- 3'ABCA4-pA transfection
4. pSSV9Kana-CMV-5'ABCA4-AP + pSSV9Kana-AP- 3'ABCA4-pA co-transfection
5. pCMV-5'ABCA4-AP-3'ABCA4-pA transfection
6. AAV5-5'ABCA4 + AAV5-3'ABCA4 co-infection
Notes:
2, 3, 4: Plasmids were linearized prior to transfection
6: AAV5 MOI was $3 \times 10^5$ vg/cell
Figure 4

A.
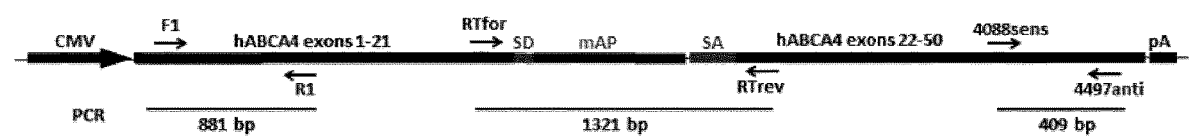
B.
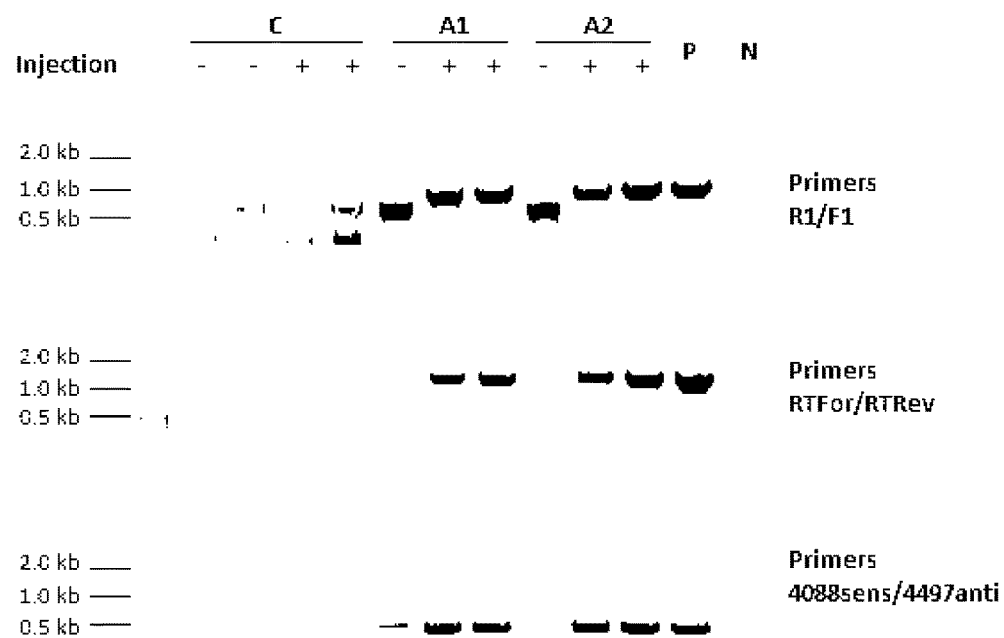
Figure 6

A.
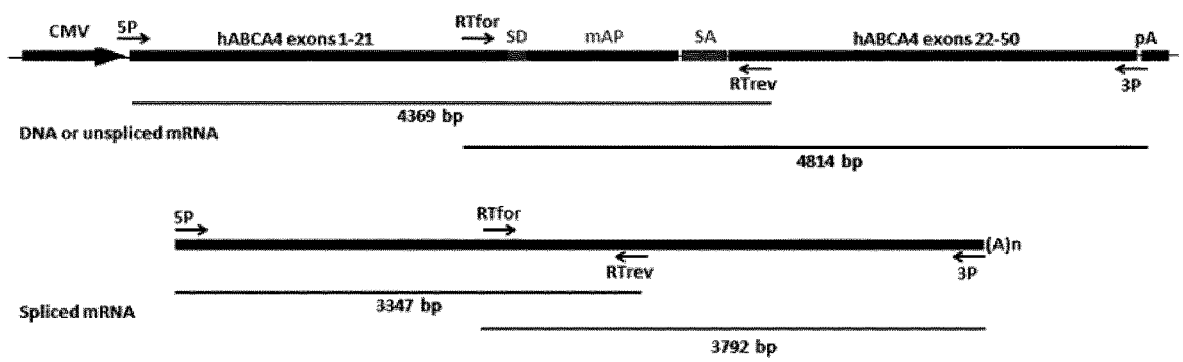
B.
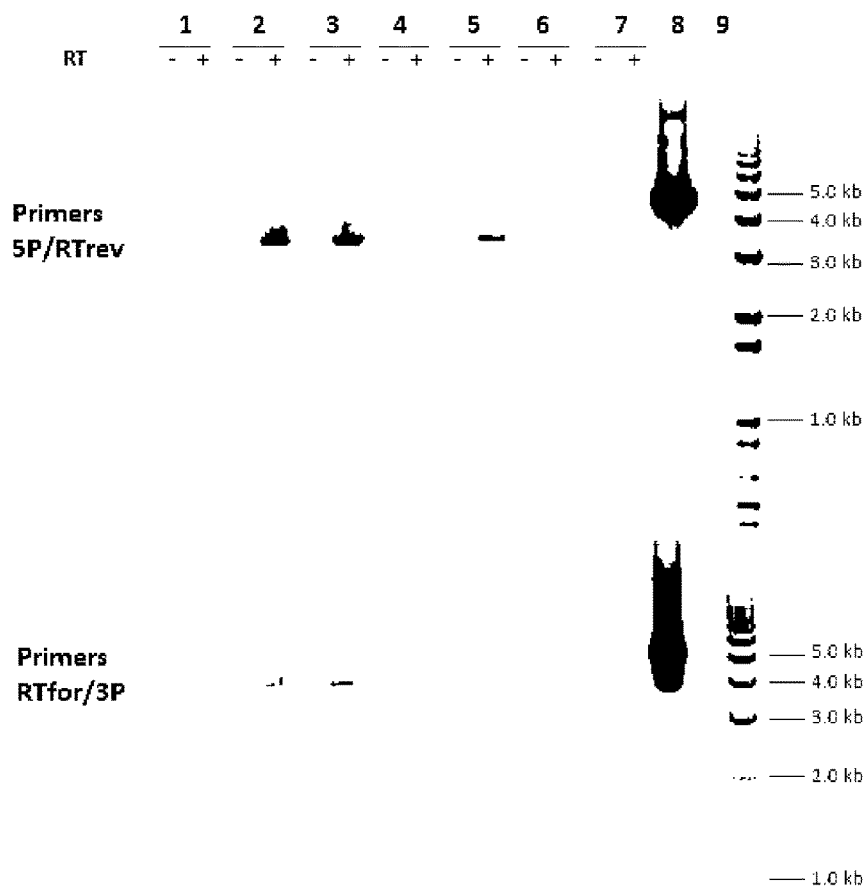
Figure 7

HYBRID DUAL RECOMBINANT AAV VECTOR SYSTEMS FOR GENE THERAPY

CROSS-REFERENCE TO RELATED APPLICATION

This application is the U.S. national stage application of International Patent Application No. PCT/EP2016/082149, filed Dec. 21, 2016.

The Sequence Listing for this application is labeled "Seq-List.txt" which was created on Jun. 14, 2018 and is 51 KB. The entire content of the sequence listing is incorporated herein by reference in its entirety.

FIELD OF THE INVENTION

The invention relates to constructs, vectors, relative host cells and pharmaceutical compositions which allow an effective gene therapy, in particular of genes larger than 5 Kb.

BACKGROUND OF THE INVENTION

Adeno-associated virus (AAV) is a small virus which infects humans and some other primate species. While AAV-mediated gene therapy is effective in animal models and in patients with inherited blinding conditions, its application to diseases affecting the retina and requiring a transfer of genes larger than 5 kb (referred to as large genes) is inhibited by AAV limited cargo capacity. To overcome this, various AAV-based strategies for large gene transduction have been developed including AAV Oversize (OZ) vectors and dual AAV strategies such as dual AAV overlapping (OV), AAV trans-splicing (TS) and AAV hybrid (with recombinogenic sequences AP or AK) vector systems.

Notably, AAV dual hybrid vector system for gene therapy of ocular diseases have been described in the international patent applications no WO 2013/075008 and WO 2014/170480. Remarkably, the in vitro and in vivo results presented in the international patent applications no WO 2014/170480 show that the AAV dual hybrid AK surprisingly outperforms the dual AAV hybrid AP and that all dual AAV strategies the inventors tested (with the exception of the dual AAV hybrid AP) outperform AAV OZ vectors in terms of transduction levels. Indeed quantification of transgene expression showed that the dual AAV hybrid AP approach resulted in the lowest levels of transgene expression, while the dual AAV OV, TS and hybrid AK approaches were more efficient than the AAV OZ approach.

Dual hybrid AK approach thus drives efficient large gene reconstitution in photoreceptors (PR) and retinal pigment epithelium (RPE). Administration of dual hybrid AK vectors improved the retinal phenotype of mouse models of STGD and USH1B, providing evidence of the efficacy of these strategies for gene therapy for these and other blinding conditions, which require large gene transfer to PR as well as RPE.

SUMMARY OF THE INVENTION

The invention relates to constructs, vectors, relative host cells and pharmaceutical compositions which allow an effective gene therapy. In particular, the invention is defined by claims.

DETAILED DESCRIPTION OF THE INVENTION

The invention relies on the unexpected discovery that a new dual construct comprising the recombinogenic region AP overcomes the previously described problems encountered with dual AAV hybrid AP, such dimeric construct leading to an optimal expression of the full-length transcripts in retinal cells, subsequently to the recombinaison/transcription/splicing process occurring with hybrid dual AAV vector system.

Accordingly, the inventors observed a significant improvement in full-length ABCA4 mRNA production in retinal cells based on said improved dual AAV hybrid AP system comprising this newly-designed dual construct composed a pair of nucleic acid sequences:

(a) a first nucleic acid sequence comprising:
the 5' end portion of a nucleic acid sequence of a synthetic intron comprising a nucleic acid sequence of a splicing donor (SD) signal (SEQ ID NO: 1), and
a nucleic acid sequence of a recombinogenic region AP; and (b) a second nucleic acid sequence comprising:
a nucleic acid sequence of a recombinogenic region AP, and
the 3' end portion of a nucleic acid sequence of a synthetic intron comprising a branch site and a polypyrimidine tract and a nucleic acid sequence of a splicing acceptor (SA) signal (SEQ ID NO: 2).

Definitions

Throughout the specification, several terms are employed and are defined in the following paragraphs.

As used herein, the term "Adeno-Associated Virus" (AAV) refers to a small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 12 recognized serotypes of AAV (AAV1-12).

As used herein, the term "Vector" refers to a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

As used herein, the term "recombinant AAV vector" (rAAV vector) refers to an AAV vector carrying a nucleic acid sequence encoding a functional gene (i.e. a polynucleotide of interest) for the genetic transformation of a retinal cell in a patient having a deleterious mutation in said gene. The rAAV vectors contain 5' and 3' adeno-associated virus inverted terminal repeats (ITRs), and the polynucleotide of interest operatively linked to sequences, which regulate its expression in a target cells, within the context of the invention, preferably or specifically in the retinal cells (photoreceptors (PR) and retinal pigment epithelium (RPE)).

As used herein, the term "Inverted Terminal Repeat" (ITR) refers to symmetrical nucleic acid sequences in the genome of adeno-associated viruses required for efficient replication and encapsidation. ITR sequences are located at each end of the AAV DNA genome. The ITRs serve as the origins of replication for viral DNA synthesis and are essential cis components for generating AAV vectors.

As used herein, the term "hybrid dual rAAV (hdrAAV) vector system" refers to a particular rAAV-based dual vector system that provide elements for expression of full-length proteins whose coding sequence exceeds the polynucleotide packaging capacity of individual rAAV vector. Indeed, the gene content of a rAAV vector was found to be limited to approximately 5 kB of DNA. Such hdrAAV vector systems have been developed as a universal platform to double the packaging capacity of recombinant AAV. In this system, the expression cassette is split into two independent AAV vectors. A highly recombinogenic bridging DNA sequence is included in both vectors to mediate target gene-independent homologous recombination between the split vector genomes. Such hdrAAV vector systems have been described in the international patent applications no WO 2013/075008 and WO 2014/170480.

A "coding sequence" is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence. Accordingly, the vector comprise regulatory sequences allowing expression and, secretion of the encoded protein, such as e.g., a promoter, enhancer, polyadenylation signal, internal ribosome entry sites (IRES), sequences encoding protein transduction domains (PTD), and the like. In this regard, the vector comprises a promoter region, operably linked to the polynucleotide sequence of interest, to cause or improve expression of the protein in infected cells. Such promoter may be ubiquitous, tissue-specific, strong, weak, regulated, chimeric, inducible, etc., to allow efficient and suitable (preferential) expression of the protein in the infected cells. The preferred promoters for use in the invention should be functional in retinal cells such as photoreceptor cells and retinal pigment epithelium (RPE) cells.

A first nucleic acid sequence is "operably linked" with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

As used herein, the term "Codon-optimized" refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

As used herein, the term "Intron" refers to a stretch of DNA within a gene that usually does not contain coding information for a protein. Introns are removed before translation of a messenger RNA by a process called RNA splicing. Thus, spliceosomal introns often reside within the sequence of eukaryotic protein-coding genes. Within the intron, a donor site (5' end of the intron), a branch site (near the 3' end of the intron) and an acceptor site (3' end of intron) are required for splicing. The splice donor site includes an almost invariant sequence GU at the 5' end of the intron, within a larger, less highly conserved region. The splice acceptor site at the 3' end of the intron terminates the intron with an almost invariant AG sequence. Upstream (5'-ward) from the AG is a region with high pyrimidines (C and U) content, or polypyrimidine tract. Upstream from the polypyrimidine tract is the branchpoint, which includes an adenine nucleotide.

As used herein, the term "Synthetic" is intended as produced by artificial means, for example a synthetic nucleic acid can be chemically or enzymatically synthesized in a laboratory.

Dual Constructs According to the Invention

In a first aspect, the invention relates to a dual construct composed a pair of nucleic acid sequences:
 (a) a first nucleic acid sequence comprising:
  the 5' end portion of a nucleic acid sequence of a synthetic intron comprising a nucleic acid sequence of a splicing donor (SD) signal (SEQ ID NO: 1), and
  a nucleic acid sequence of a recombinogenic region; and
 (b) a second nucleic acid sequence comprising:
  a nucleic acid sequence of a recombinogenic region, and
  the 3' end portion of a nucleic acid sequence of a synthetic intron comprising a branch site and a polypyrimidine tract and a nucleic acid sequence of a splicing acceptor (SA) signal (SEQ ID NO: 2).

In one embodiment of the invention, the recombinogenic region is a polynucleotide sequence derived or originating from alkaline phosphatase (AP) or from bacteriophage F1 (AK), or other polynucleotide sequences known as a homologous recombination hotspot such as sequence derived or originating from minisatellite DNA or MHC recombination hotspot, or the like.

In a particular embodiment of the invention, the recombinogenic region AP has the sequence SEQ ID NO: 3 or a fragment thereof (SEQ ID NO: 4=⅓ head or SEQ ID NO: 5=⅓ tail) or still preferably a derived codon-modified (mAP) sequence SEQ ID NO: 6, into which all ATG codons on both DNA strands (except one) were removed.

A Hybrid Dual Construct System According to the Invention

In a second aspect, the invention relates to an to a hybrid dual construct system suitable for expressing the coding sequence of a gene of interest in an host cell, comprising:
 a) a first polynucleotide comprising in a 5'-3' direction:
  a 5'-inverted terminal repeat (5'-ITR) sequence;
  a promoter sequence;
  the 5' end portion of said coding sequence, said 5' end portion being operably linked to and under control of said promoter;
  the 5' end portion of a sequence of a synthetic intron comprising a nucleic acid sequence of a splicing donor (SD) signal (SEQ ID NO: 1);
  a nucleic acid sequence of a recombinogenic region; and
  a 3'-inverted terminal repeat (3'-ITR) sequence; and
 b) a second polynucleotide comprising in a 5'-3' direction:
  a 5'-inverted terminal repeat (5'-ITR) sequence;
  a nucleic acid sequence of a recombinogenic region;
  the 3' end portion of a sequence of a synthetic intron comprising a branch site, a polypyrimidine tract and a splicing acceptor (SA) signal (SEQ ID NO: 2);
  the 3' end of said coding sequence;
  a poly-adenylation (pA) signal nucleic acid sequence; and
  a 3'-inverted terminal repeat (3'-ITR) sequence.

Upon introduction of said first polynucleotide and said second polynucleotide into the host cell, said coding sequence reconstitutes by means of (1) recombination between both polynucleotides to form a single DNA molecule, (2) transcription and (3) splicing between the splicing donor (SD) and the splicing acceptor (SA) signals.

In one embodiment of the invention, the coding sequence is a nucleotide sequence encoding a protein able to correct an inherited retinal degeneration.

The desired gene together with a promoter to drive transcription of the gene is inserted between the inverted terminal repeats (ITR) that aid in concatemer formation in the nucleus after the single-stranded vector DNA is converted by host cell DNA polymerase complexes into double-stranded DNA. AAV-based gene therapy vectors form episomal concatemers in the host cell nucleus. In non-dividing cells, these concatemers can remain intact for the life of the host cell. In dividing cells, AAV DNA is lost through cell division, since the episomal DNA is not replicated along with the host cell DNA.

In one embodiment, the nucleotide sequence of the ITRs derives from the same AAV serotype or from different AAV serotypes.

In one embodiment, the 3'-ITR of the first plasmid and the 5'-ITR of the second plasmid are from the same AAV serotype.

In one embodiment, the 5'-ITR and 3'-ITR of the first plasmid and the 5'-ITR and 3'-ITR of the second plasmid are respectively from different AAV serotypes.

In one embodiment, the 5'-ITR of the first plasmid and the 3'-ITR of the second plasmid are from different AAV serotypes.

Preferably the coding sequence is a nucleotide sequence encoding a protein able to correct a genetic disease, in particular an inherited retinal degeneration. Still preferably the coding sequence is selected from the group consisting of ABCA4, MY07A, CEP290, CDH23, EYS, USH2A, GPR98 and ALMS1 genes. In a particular embodiment of the invention, the coding sequence of a gene of interest is the sequence of the ABCA4 gene.

In the present invention, the coding sequence is split into a first and a second fragment (5' end portion and 3' end portion) at a natural exon-exon junction.

Preferably each fragment of the coding sequence should not exceed a size of 5.2 kb. Preferably each 5' end portion and 3' end portion may have a size of 2.5 Kb, 3.0 Kb, 3.5 Kb, 4.5 Kb, 5 Kb, or a smaller size.

Accordingly, in a particular embodiment of the invention, the 5' end portion of the coding sequence of ABCA4 gene has the sequence SEQ ID NO: 7 (exons 1-21) and the 3' end of said coding sequence of ABCA4 gene has the sequence SEQ ID NO: 8 (exons 22-50).

In one embodiment of the invention, the promoter sequence is the human cytomegalovirus (CMV) promoter or the human rhodopsin kinase (RK) promoter (also referred as GRK1 (G-coupled receptor kinase 1) or RHOK).

In a preferred embodiment of the invention, the first polynucleotide comprises the sequence SEQ ID NO: 9 (CMV-5'ABCA4-SD-AP) or SEQ ID NO: 10 (RK-5'ABCA4-SD-AP), and the second polynucleotide comprises the sequence SEQ ID NO: 11 (AP-SA-3'ABCA4-pA).

An Hybrid Dual rAAV Vector System According to the Invention

In a third aspect, the invention relates to a hybrid dual rAAV (hdrAAV) vector system suitable for expressing the coding sequence of a gene of interest in a host cell, comprising:

a) a first rAAV vector containing a first polynucleotide comprising in a 5'-3' direction:
  a 5'-inverted terminal repeat (5'-ITR) sequence;
  a promoter sequence;
  the 5' end portion of said coding sequence, said 5' end portion being operably linked to and under control of said promoter;
  the 5' end portion of a sequence of a synthetic intron comprising a nucleic acid sequence of a splicing donor (SD) signal (SEQ ID NO: 1);
  a nucleic acid sequence of a recombinogenic region; and
  a 3'-inverted terminal repeat (3'-ITR) sequence;
  and
b) a second rAAV vector containing a second polynucleotide comprising in a 5'-3' direction:
  a 5'-inverted terminal repeat (5'-ITR) sequence;
  a nucleic acid sequence of a recombinogenic region;
  the 3' end portion of a sequence of a synthetic intron comprising a branch site and a polypyrimidine tract (SEQ ID NO: 2);
  a nucleic acid sequence of a splicing acceptor (SA) signal;
  the 3' end of said coding sequence;
  a poly-adenylation signal nucleic acid sequence; and
  a 3'-inverted terminal repeat (3'-ITR) sequence.

In one embodiment of the invention, the recombinant AAV vectors are selected from the serotype 2, the serotype 4, the serotype 5 and the serotype 8.

In a preferred embodiment of the invention, the first rAAV vector comprises the sequence SEQ ID NO: 12 (AAV-CMV-5'ABCA4-SD-mAP vector) or SEQ ID NO: 13 (AAV-RK-5'ABCA4-mAP vector), and the second rAAV vector comprises the sequence SEQ ID NO: 14 (AAV-mAP-SA-3'ABCA4-pA vector).

The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. The former is composed of four overlapping genes encoding Rep proteins required for the AAV life cycle, and the latter contains overlapping nucleotide sequences of capsid proteins: VP1, VP2 and VP3, which interact together to form a capsid of an icosahedral symmetry. The Inverted Terminal Repeat (ITR) sequences comprise 145 bases each. They were named so because of their symmetry, which was shown to be required for efficient replication of the AAV genome. Another property of these sequences is their ability to form a hairpin, which contributes to so-called self-priming that allows primase-independent synthesis of the second DNA strand. The ITRs were also shown to be required for both integration of the AAV DNA into the host cell genome (19th chromosome in humans) and rescue from it, as well as for efficient encapsidation of the AAV DNA combined with generation of a fully assembled, deoxyribonuclease-resistant AAV particle. With regard to gene therapy, ITRs seem to be the only sequences required in cis next to the therapeutic gene: structural (cap) and packaging (rep) genes can be delivered in trans for vector assembly in the producer cells.

The rAAV vectors such as an rAAV2/5 vector as described below are produced using methods known in the art. In short, the methods generally involve the introduction into a host cell of (a) the rAAV vector, (b) an AAV trans-complementing construct comprising the viral rep and cap genes missing from the rAAV vector and (c) a helper construct comprising AAV helper functions from a helper virus. All functions for AAV capsid assembly, rAAV DNA replication and packaging need to be present, to achieve replication and packaging of the rAAV vector into rAAV virions. The introduction into the host cell can be carried out using standard biological techniques simultaneously or sequentially. Finally, the host cells are cultured to produce rAAV virions, which are then purified using different methods, including standard techniques such as CsCl gradients or more advanced techniques such as ion-exchange chromatography. The purified rAAV virion is then ready for use in the methods.

Host Cells According to the Invention

As used herein, the term "host cell or host cell genetically engineered" relates to host cells which have been transduced, transformed or transfected with the construct or with the vector as described previously. As representative examples of appropriate host cells, one can cites bacterial cells, such as *E. coli, Streptomyces, Salmonella typhimurium*, fungal cells such as yeast, insect cells such as Sf9, animal cells such as CHO or COS, plant cells, etc. The selection of an appropriate host is deemed to be within the scope of those skilled in the art from the teachings herein. Preferably, said host cell is an animal cell, and most preferably a human cell. The invention further provides a host cell comprising any of the recombinant expression vectors described herein. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5alpha *E. coli* cells, Chinese hamster ovarian (CHO) cells, monkey VERO cells and COS cells, human HEK293 and HeLa cells, and the like.

Pharmaceutical Compositions According to the Invention

A fourth aspect of the invention relates to a pharmaceutical composition comprising the hybrid dual construct system according to the invention, the hybrid dual viral vector system according to the invention or the host cell according to the invention and a pharmaceutically acceptable vehicle.

The pharmaceutical composition may be for human or animal usage. Typically, a physician will determine the actual dosage which will be most suitable for an individual subject and it will vary with the age, weight and response of the particular individual.

Preferably, the rAAV vectors containing the desired transgene as detailed above is preferably assessed for contamination by conventional methods and then formulated into a pharmaceutical composition intended for subretinal injection. Such formulation involves the use of a pharmaceutically and/or physiologically acceptable vehicle or carrier, particularly one suitable for administration to the eye, e.g., by subretinal injection, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, etc. For injection, the carrier will typically be a liquid. Exemplary physiologically acceptable carriers include sterile, pyrogen-free water and sterile, pyrogen-free, phosphate buffered saline. The precise nature of the carrier or other material may be determined by the skilled person according to the route of administration, i.e. here the subretinal injection. Such materials should be non-toxic and should not interfere with the efficacy of the active ingredient (i.e. the rAAV vectors of the invention).

Methods of Treatment According to the Invention

A fifth aspect of the invention relates to the hybrid dual construct system of the invention, the hybrid dual viral vector system of the invention or the host cell of the invention for use as drug, preferably for use in a gene therapy, still preferably for a method of treatment and/or prevention of a pathology or disease characterized by a retinal degeneration.

Accordingly, the invention relates to a method of treatment and/or prevention of a pathology or disease characterized by a retinal degeneration in a subject in need thereof, comprising a step of administering a therapeutically effective amount of the hybrid dual construct system of the invention, the hybrid dual viral vector system of the invention or the host cell of the invention.

Preferably, the retinal degeneration is inherited. Still preferably the pathology or disease is selected from the group consisting of Retinitis Pigmentosa (RP), Leber congenital amaurosis (LCA), Stargardt disease, Usher syndrome, Alstrom syndrome, a disease caused by a mutation in the ABCA4 gene (also named a ABCA4-associated disease). Stargardt disease, cone-rod dystrophy type 3, fundus flavimaculatus, age-related macular degeneration type 2, Early-onset severe retinal dystrophy, and Retinitis pigmentosa type 19 are examples of disease caused by a mutation in the ABCA4 gene (ABCA4-associated diseases).

A seventh aspect relates to a method for treating and/or preventing a pathology or disease characterized by a retinal degeneration comprising administering to a patient in need thereof an effective amount of the hybrid dual construct system as described herein, the hybrid dual viral vector system as described herein or the host cell as described herein.

As used herein, the term "patient" is intended for a human. Typically the patient is affected or likely to be affected with an inherited retinal degenerative disorder, affecting the retinal pigment epithelium (RPE) cells or the photoreceptors cells. For instance, patients are candidates for the methods of treatment include those who have a diagnosis of LCA or Stargardt disease. Originally described by Leber in 1869, LCA is an autosomal recessive disease distinct from other retinal dystrophies and responsible for congenital blindness. Leber congenital amaurosis (LCA) (MIM 204000) is characterized by severe or complete loss of visual function apparent early in infancy with failure to follow visual stimuli, nystagmus, and roving eye movements. Affected individuals have an extinguished electroretinogram and eventually develop abnormalities of the ocular fundus including a pigmentary retinopathy. LCA is a severe childhood-onset blinding disease which may be caused by mutations in more than 10 genes. One of the most frequently mutated genes is CEP290.

Stargardt disease, also known as fundus flavimaculatus, is the most common form of inherited juvenile macular degeneration. It is characterized by a reduction of central vision with a preservation of peripheral (side) vision. Stargardt disease is almost always inherited as an autosomal recessive disorder. The gene responsible for Stargardt disease has been identified as the ABCA4 gene, which encodes the ABCR protein. ABCR stands for "ATP-binding cassette transporter-retinal". The ABCR protein plays an important role in the visual cycle: All-trans retinal, which is released into the disc lumen of the photoreceptor cells, reacts with phosphatidyl ethanolamine (PE) to N-retinylidene-PE, which is subsequently transported into the cytosol by the function of the ABCR. Thus, ABCR is the rate keeper of retinal transport in the visual cycle. If ABCR function is lost, N-retinylidene-PE accumulates in the disc lumen. Once the discs are phagocytosed by Retinal Pigment Epithelium (RPE) cells, excessive N-retinylidene-PE is transformed into N-retinylidine-N-retinylethanolamine (A2-E), which is a major component of lipofuscin. Accumulation of lipofuscin leads to RPE cell apoptosis. Thus, mutations in the ABCR gene produce a dysfunctional protein that cannot perform its transport function. As a result, photoreceptor cells degenerate and vision loss occurs. The most common mutations, accounting for 10% of all cases of autosomal recessive Stargardt Disease, are G1961E, G863A, [Delta]G863, and A1038V.

In certain embodiments of the invention it is desirable to perform non-invasive retinal imaging and functional studies to identify areas of retained photoreceptors to be targeted for therapy. In these embodiments, clinical diagnostic tests are employed, to determine the precise location(s) for one or more subretinal injection(s). These tests may include electroretinography (ERG), perimetry, topographical mapping of the layers of the retina and measurement of the thickness of its layers by means of confocal scanning laser ophthalmoscopy (eSLO) and optical coherence tomography (OCT), topographical mapping of cone density via adaptive optics (AO), functional eye exam, etc.

In view of the imaging and functional studies, the volume and viral titer of each injection is determined individually, as further described below, and may be the same or different from other injections performed in the same, or contralateral, eye.

By "effective amount" is meant an amount sufficient to achieve a concentration of rAAV vectors which is capable of preventing, treating or slowing down the disease to be treated. Such concentrations can be routinely determined by those skilled in the art. The amount of the rAAV composition actually administered will typically be determined by a physician, in the light of the relevant circumstances, including the disease to be treated, the chosen route of administration, the age, weight, and response of the patient, the severity of the patient's symptoms, and the like. It will also be appreciated by those skilled in the art that the dosage may be dependent on the stability of the administered rAAV vector.

In one embodiment, the volume and concentration of the rAAV vectors is selected so that only the region of damaged retinal cells such as the photoreceptors is impacted. In another embodiment, the volume and/or concentration of the rAAV vectors is a greater amount, in order to reach larger portions of the eye, including non-damaged photoreceptors.

The pharmaceutical composition may be delivered in a volume of from about 50 µL to about 1 mL, including all numbers within the range, depending on the size of the area to be treated, the viral titer and the desired effect of the method. In one embodiment, the volume is about 50 µL. In another embodiment, the volume is about 100 µL. In another embodiment, the volume is about 150 µL. In yet another embodiment, the volume is about 200 µL. In another embodiment, the volume is about 250 µL. In another embodiment, the volume is about 300 µL. In another embodiment, the volume is about 400 µL. In another embodiment, the volume is about 450 µL. In another embodiment, the volume is about 500 µL. In another embodiment, the volume is about 600 µL. In another embodiment, the volume is about 750 µL. In another embodiment, the volume is about 800 µL. In another embodiment, the volume is about 900 µL. In yet another embodiment, the volume is about 1000 µL.

The doses of vectors may be adapted depending on the disease condition, the patient, the treatment schedule, etc. A preferred effective dose within the context of this invention is a dose allowing an optimal transduction of the photoreceptors and/or RPE cells. Typically, from $10^8$ to $10^{10}$ viral genomes (vg) are administered per dose in mice. Typically, the doses of AAV vectors to be administered in humans may range from $10^{10}$ to $10^{12}$ vg.

Accordingly, an effective concentration of a recombinant adeno-associated virus carrying a nucleic acid sequence encoding the desired transgene desirably ranges between about $10^8$ and $10^{14}$ vector genomes per milliliter (vg/mL). Preferably, the concentration is from about $1 \times 10^9$ vg/mL to about $1 \times 10^{13}$ vg/mL, and more preferably from about $1 \times 10^{11}$ vg/mL to about $1 \times 10^{12}$ vg/mL. In one embodiment, the effective concentration is about $5 \times 10^{11}$ vg/mL.

The invention will be further illustrated by the following figures and examples. However, these examples and figures should not be interpreted in any way as limiting the scope of the present invention.

FIGURES

FIG. 1. Schematic representation of the 5' and 3' hybrid dual AAV vector genomes for ABCA4 gene transfer.

Figure 2:
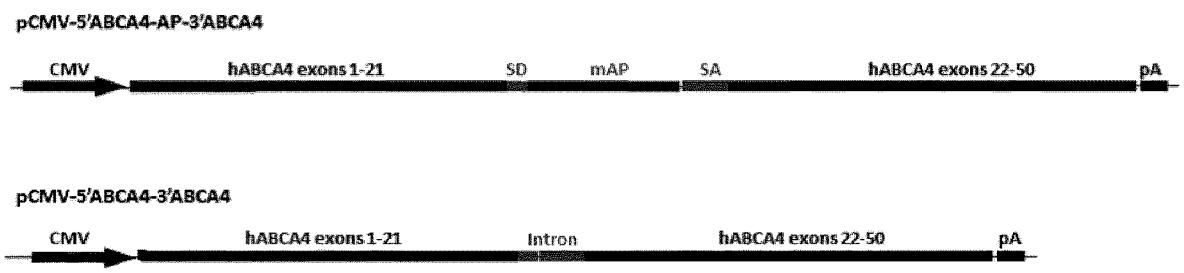

FIG. 2. Schematic representation of the control plasmids for ABCA4 expression in vitro.

FIG. 3. Detection of AAV-5'ABCA4 and AAV-3'ABCA4 vector recombination in vitro by PCR. (A) Schematic representation of the expected DNA sequence and PCR amplicons for AP-mediated recombination products and for control plasmid pCMV-5'ABCA4-mAP-3'ABCA4-pA (upper picture), and for control plasmid pCMV-5'ABCA4-3'ABCA4-pA (lower picture). Arrows represent RTfor and RTrev PCR primers, and size of the expected PCR products are indicated. (B) Detection of ABCA4 5'/3' junctions by PCR in COST cells following plasmid transfection or AAV2/5 infection.

FIG. 4. Detection of ABCA4 mRNA in vitro by RT-PCR. (A) Schematic representation of the expected sequence for DNA and unspliced RNA (upper picture) and for the spliced polyA+ mRNA (lower picture). PCR primers are indicated by arrows and expected PCR products are shown with their size indicated. (B) Detection of ABCA4 mRNA expression by RT-PCR in HEK293 cells following plasmid transfection or AAV2/5 infection.

Figure 5:
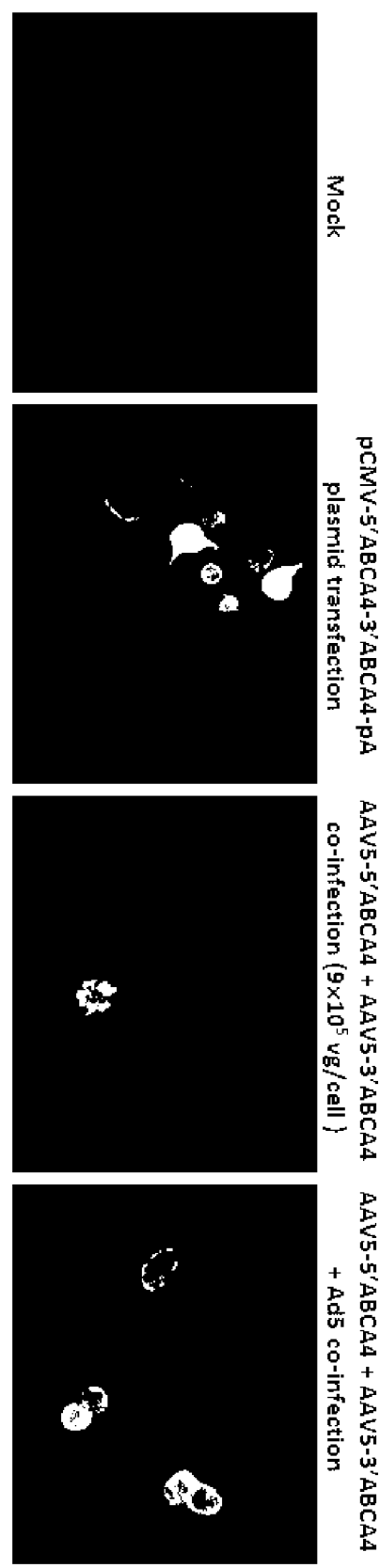

FIG. 5. Detection of ABCA4 protein expression by immuno-fluorescence staining on HeLa cells following plasmid transfection or AAV2/5 infection (+/−Ad5).

FIG. 6. Detection of the dual ABCA4 vectors DNA by PCR following intra-muscular injection in C57/BL6 mice. (A) Schematic representation of the expected DNA sequence and PCR amplicons for dual AAV AP-mediated recombination products and for control plasmid pCMV-5'ABCA4-mAP-3'ABCA4-pA Arrows represent PCR primers, and size of the expected PCR products are indicated. (B) PCR results obtained with mouse muscles injected injected or not with the dual AAV5-ABCA4 vectors. Samples were: control mouse injected with PBS (C), mice injected with the dual AAV5-ABCA4 vectors (A1 and A2), non-injected or injected muscles (− or +), pCMV-5'ABCA4-mAP-3'ABCA4 plasmid DNA (P), and no template control (N).

FIG. 7. Detection of ABCA4 mRNA by RT-PCR following intra-muscular injection of the dual AAV5-ABCA4 vectors in C57/BL6 mice. (A) Schematic representation of the expected sequence for DNA and unspliced RNA (upper picture) and for the spliced polyA+ mRNA (lower picture). PCR primers are indicated by arrows and expected PCR products are shown with their size indicated. (B) RT-PCR results obtained with mouse muscles injected or not with the dual AAV5-ABCA4 vectors. Samples were: mouse A1 non-injected (1) and dual AAV injected muscles (2 and 3), mouse A2 non-injected (4) and dual AAV injected muscles (5 and 6), mouse C non-injected muscle (7), pCMV-5'ABCA4-mAP-3'ABCA4 plasmid DNA (8), and no template control (9). Muscle RNA samples were reverse transcribed (+) or not (−) with M-MLV RT prior to PCR.

Figure 8:
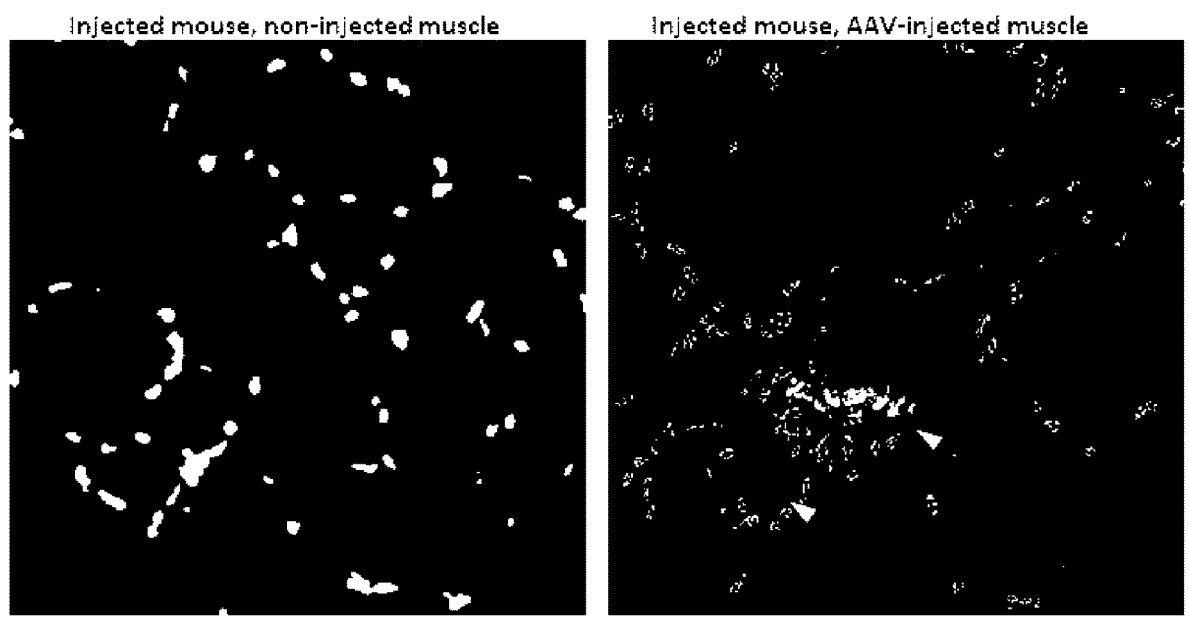

FIG. 8. Detection of ABCA4 protein expression by immuno-fluorescence staining of muscle cryosection following intra-muscular injection of the dual AAV5 ABCA4 vectors in C57/BL6 mice. Cell nuclei appear in grey and the ABCA4 protein in white (ABCA4-positive muscle fibers indicated by white arrows).

Figure 9:
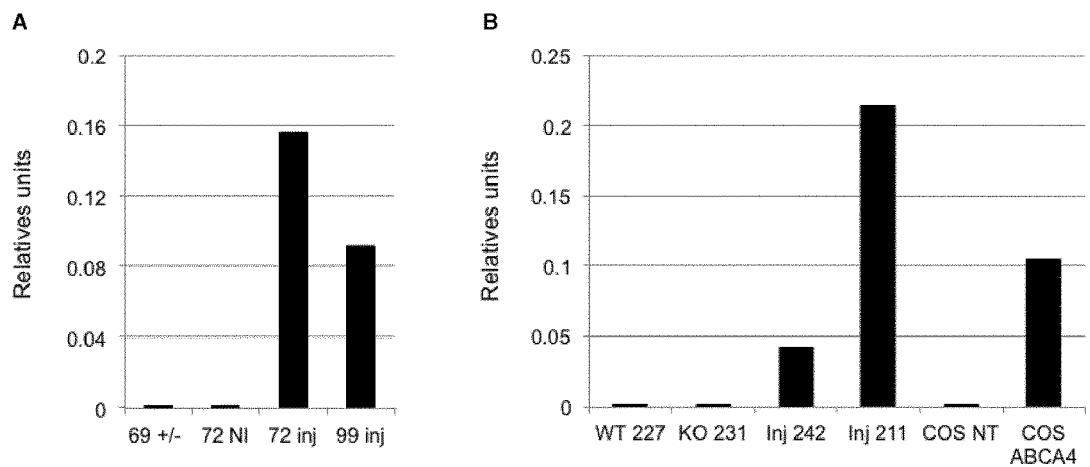

FIG. 9. Human ABCA4 transcript is detected by RT-qPCR analysis of injected Abca4$^{−/−}$ mouse eyes in two independent experiments. A) Five weeks post-injection of the dual AAV2/5 ABCA4 vectors, an ABCA4 transcript was detected in the neuroretina of injected Abca4$^{−/−}$ mice (72 Inj; 99 Inj). No transcript was detected in the neuroretinas from control Abca4$^{+/−}$ (69+/−) and non-injected Abca4$^{−/−}$ (71 NI) mice. B) Four weeks post-injection of the dual AAV2/5 ABCA4 vectors, an ABCA4 transcript was detected in the neuroretina of injected Abca4$^{−/−}$ mice (Inj 242; Inj 211). No transcript was detected in the neuroretinas from control Abca4$^{+/+}$ (WT 227) and non-injected Abca4$^{−/−}$ (KO 231) mice. As a positive control for the qPCR reaction, an ABCA4 transcript was detected in COS cells transfected with the plasmid pCMV-5'ABCA4-3'ABCA4-pA (COS ABCA4) as compared to non-transfected (NT) cells.

Figure 10:
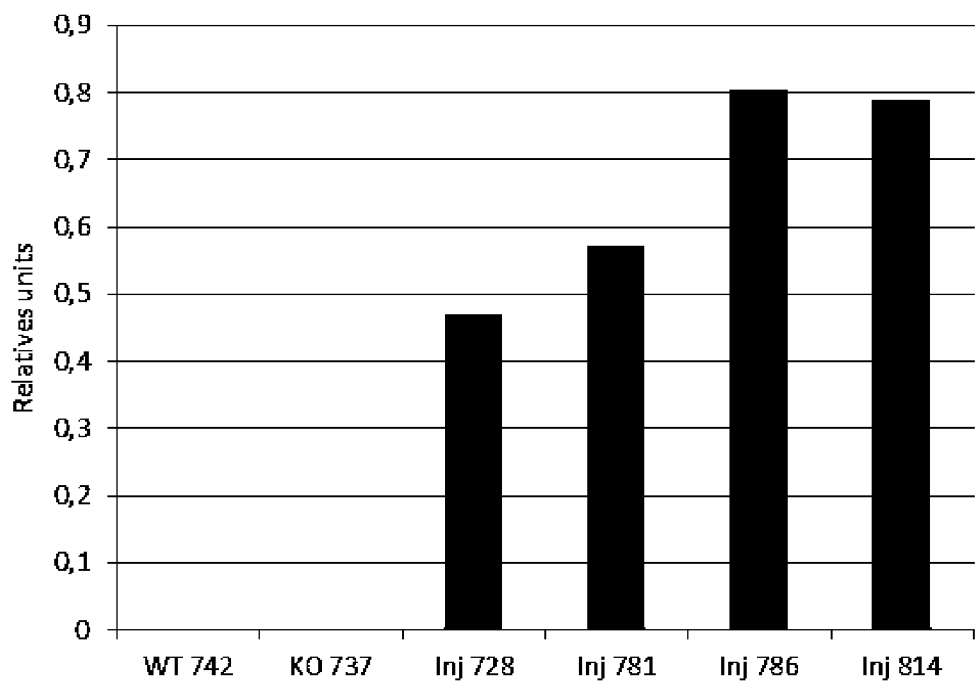

FIG. 10. Human ABCA4 transcript is detected by RT-qPCR analysis of injected Abca4$^{−/−}$ mouse eyes using different vector combinations. Seven weeks post-injection of the dual AAV2/5 ABCA4 vectors, a human ABCA4 transcript was detected in the neuroretina of injected Abca4$^{−/−}$ mice (Inj 728, -781, -786, -814). Mice 728 and 781 were injected with the CMV-5'ABCA4-mAP vector and the mAP-3'ABCA4 vector. Mice 786 and 814 were injected with the RK-5'ABCA4-mAP vector and the mAP-3'ABCA4 vector. No transcript was detected in the neuroretinas of control Abca4$^{+/+}$ (WT 742) and non-injected Abca4$^{−/−}$ (KO 737) mice.

Figure 11:
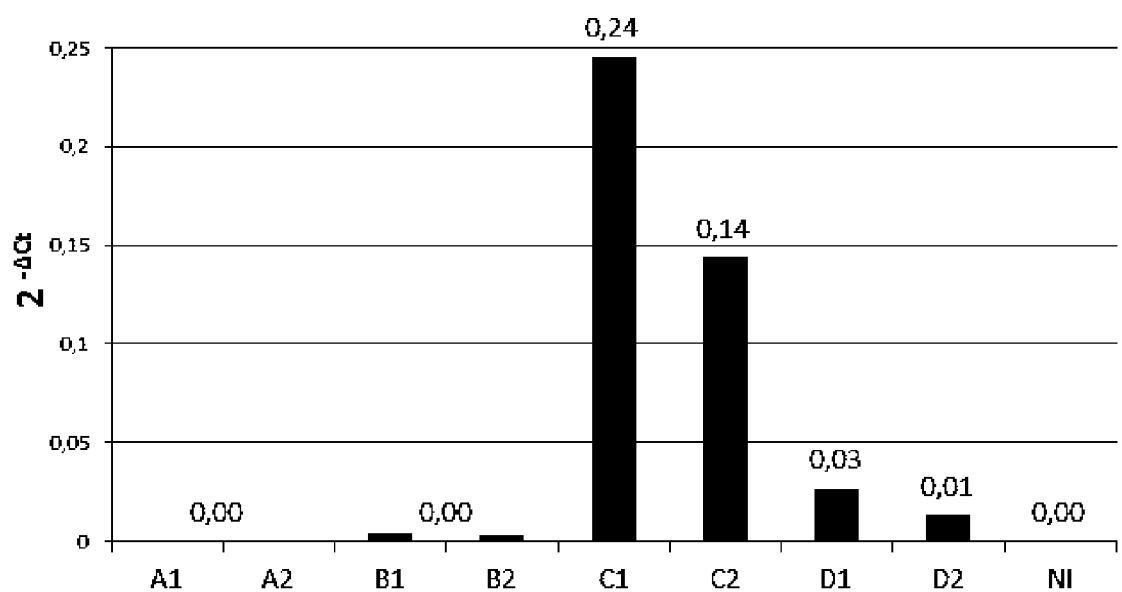

FIG. 11. Human ABCA4 transcript is detected by RT-qPCR analysis of injected rat eyes using different vector combinations. Eight weeks after vector injections, a human ABCA4 transcript was detected in the neuroretina of rats injected with the dual AAV2/5 ABCA4 vectors. Rats C1 and C2 were injected with the RK-5'ABCA4-mAP vector and the mAP-3'ABCA4 vector. Rats D1 and D2 were injected with the CMV-5'ABCA4-mAP vector and the mAP-3'ABCA4 vector. No transcript was detected in the neuroretina of rats injected with the RK-5'ABCA4-mAP (A1 and A2) or the mAP-3'ABCA4 (B1 and B2) vector alone, and in the non-injected rat (NI).

EXAMPLE

Material & Methods
Plasmid Constructions:
The split ABCA4 coding sequence (from Genbank NM_000350.2), the intronic sequences, the AP-derived recombinogenic sequence and the short poly-adenylation sequence were designed in silico based on published sequences. DNA containing the designed sequences was obtained by gene synthesis.

For AAV vector construction, sequences were assembled into a kanamycin-resistant AAV-2 plasmid backbone (pSSV9Kana) by standard cloning using suitable restriction endonucleases. The ITR-flanked genome content of the vectors is described below and in FIG. 1.

For construction of the AAV-5'ABCA4 vector, the human cytomegalovirus (CMV) immediate-early enhancer/promoter from pcDNA3.1 (Invitrogen), or the human rhodopsin kinase (RK) core promoter (Khani et al., IOVS 2007), was cloned upstream of a fragment including a consensus Kozak sequence, exons 1 to 21 of the human ABCA4 coding sequence, the splice donor sequence (SD) from the chimeric intron of pCI-Neo (Promega), and a human alkaline phosphatase (AP)-derived sequence corresponding to that described by Ghosh et al. (Mol Ther 2008), except that all ATG codons on both DNA strands (but one) were removed. The overall vector genome length (from ITR to ITR) was 5166 bp with the CMV promoter or 4745 bp with the RK promoter.

For construction of the AAV-3'ABCA4 vector, the same AP-derived sequence as in the 5' vector was cloned upstream of the branch site, polypyrimidine tract and splice acceptor sequence from pCI-Neo chimeric intron (Promega), exons 22 to 50 of the human ABCA4 coding sequence, and a synthetic polyadenylation signal from pCI-Neo (Promega). The overall vector genome length (from ITR to ITR) was 5024 bp.

For functional testing of our designed ABCA4 expression system in vitro, two control plasmids were constructed into a pBlueScript plasmid backbone (FIG. 2):

Plasmid pCMV-5'ABCA4-mAP-3'ABAC4 contains the expression cassette that should be reconstituted upon homologous recombination between the 5' and 3' vectors, i.e. with the 5' and 3' parts of the ABCA4 coding sequence separated by the chimeric intron containing the AP-derived recombinogenic sequence. Plasmid pCMV-5'ABCA4-3'ABCA4 contains the same expression cassette except that the AP sequence was deleted from the intron.

AAV Vector Production:
AAV2/5 vector production was achieved by double transfection of HEK293 cells (Grimm et al., 2003). The helper plasmid used was pDP5-Kana, a derivative of pDP5rs (Grimm et al., 2003) into which ampicillin resistance was replaced with kanamycin resistance and the DsRed expression cassette was deleted. Cells grown in CellStack-5 culture chambers were co-transfected with helper plasmid pDP5-Kana together with each AAV vector plasmid (pSSV9Kana-CMV-5'ABAC4-mAP, pSSV9Kana-RK-5'ABAC4-mAP or pSSV9Kana-mAP-3'ABCA4-pA), and the AAV particles were harvested from both cells and culture supernatant at 96 h post-transfection. AAV from the supernatant was precipitated with PEG-8000, and vector particles were purified through two round of CsCl gradient ultracentrifugation as previously described (Ayuso et al., Gene Ther 2010).

Full AAV particles, i.e. encapsidated vector genomes (vg), were quantified by dot blot hybridization, and infectious AAV particles were quantified by the infectious center assay (ICA) on HeRC32 cells as previously described (Salvetti et al, Hum Gene Ther 1998). The probe used for both dot blot and ICA was generated with the PCR Fluorescein Labelling Mix (Roche), using primers hPLAP326sens and hPLAP785anti and pCMV-5'ABCA4-mAP-3'ABCA4 plasmid as the template DNA. Following hybridization, detection was performed using the CDP-Star ready-to-use labelling kit (Roche).

ABCA4 Gene Transfer In Vitro:

HEK293, HeLa and COS-7 cells were maintained in Dulbecco's modified Eagle medium (DMEM) containing 2 mM L-Glutamine and 4.5 g/L glucose (Sigma-Aldrich), supplemented with 10% fetal bovine serum (HyClone). AAV infections were performed in DMEM supplemented with 2% fetal bovine serum containing the AAV2/5 vectors, with or without adenovirus type 5. Plasmid transfection was performed by the calcium phosphate precipitation method. For PCR and RT-PCR analysis, cells were harvested 48 (with adenovirus) or 72 (without adenovirus) hours after infection or transfection and washed in 1×PBS. For PCR, total DNA was extracted using the NucleoSpin Blood kit (Macherey-Nagel). For RT-PCR, total RNA was extracted using Trizol reagent (Life Technologies). Poly-adenylated mRNA were reverse-transcribed into cDNA with M-MLV Reverse Transcriptase (Life Technologies) using oligo(dT) primers. PCR amplifications were performed on total DNA or cDNA with GoTaq DNA polymerase, using primers ABCA4-RTfor and ABCA4-RTrev (FIGS. 3.A and 4.A). For immuno-fluorescence staining, cells were fixed 72 hours after infection or transfection in PBS containing 2% paraformaldehyde, and permeabilized in PBS, 0.2% Triton X-100. Cells were then incubated with anti-ABCA4 mouse monoclonal antibody 3F4 (Santa Cruz), and then with anti-mouse AlexaFluor-488 antibody (Life technologies). Slides were finally mounted with Prolong Gold antifade reagent (Life Technologies) and observed with a Nikon Eclipse 90i microscope.

ABCA4 Gene Transfer in Mouse Muscles In Vivo:

For ABCA4 gene transfer in the skeletal muscle, a mix of AAV2/5-CMV-5'ABCA4-mAP and AAV2/5-mAP-3'ABCA4 vectors at $8.4 \times 10^{11}$ vg/mL each was injected into the tibialis anterior muscles of two 8-weeks hold C57/BL6 mice (A1 and A2). Two legs were injected with ~30 μL of vector mix, i.e. ~$2.5 \times 10^{10}$ vg of each vector per injected muscle (~$5.0 \times 10^{10}$ total vg/muscle). One control mouse (C) was injected the same way with buffer (DPBS) alone. All three mice were euthanized 1 month post-injection for analysis of injected and non-injected muscles.

For PCR analysis, total DNA was extracted from muscles samples using a TissueLyser II device (Qiagen) and Gentra Puregene reagents (Qiagen). PCR was performed with GoTaq DNA polymerase (Promega) using primers ABCA4-F1 and -R1, ABCA4-4088s and -4497as and ABCA4-RTfor and -RTrev, to detect ABCA4 5' and 3'ends as well as junctions between the 5'ABCA4 and the 3'ABCA4 vectors (FIG. 6.A).

For RT-PCR analysis, total RNA was extracted from muscles using a TissueLyser II device (Qiagen) and Trizol reagent (Life Technologies), and poly-adenylated mRNA were reverse-transcribed or not into cDNA with M-MLV Reverse Transcriptase (Life Technologies) using oligo(dT) primers. PCR was performed with KOD Xtrem DNA polymerase (Novagen) using primers ABCA4-5P and -RTrev, or ABCA4-RTfor and -3P, in order to amplify the full-length ABCA4 mRNA as two overlapping fragments (FIG. 7.A). For immuno-fluorescence microscopy analysis, muscle cryosections were fixed with 4% paraformaldehyde for 10 min at room temperature, permeabilized with 0.2% Triton X-100, and incubated in blocking buffer (20% goat serum) during 30 min. They were then incubated overnight with anti-ABCA4 mouse monoclonal antibody 3F4 (Santa Cruz), and then with anti-mouse AlexaFluor-488 antibody (Life technologies). Sections were then incubated with DRAQ5 (Biostatus Limited) to counterstain nuclei, and pictures were acquired by confocal microscopy. Stained muscle sections were mounted using Prolong Gold antifade reagent (Life Technologies) and observed with a Nikon Eclipse TE-2000 confocal microscope.

ABCA4 Gene Transfer in the Mouse Retina:

Abca4$^{-/-}$ mice, generated by replacing exon 1 of the Abca4 gene by a LacZ/neo cassette, were purchased from Lexicon Pharmaceuticals. All animal breeding and experiments were carried out in accordance with the European and National guidelines for the care and use of laboratory animals (Council Directive 86/6009/EEC). For subretinal injections, eight-week-old mice were anesthetized with 70 mg/kg ketamine and 28 mg/kg xylazine and the pupils were dilated with a drop of 0.5% tropicamide (Mydiatricum, Théa). The cornea was covered with a drop of Lacryvisc (Alcon) and a glass-coverslip. Under a surgical microscope, a mix of 1.4 to $2.8 \times 10^9$ vg of AAV2/5-CMV-5'ABCA4-mAP and 1.2 to $2.4 \times 10^9$ vg of AAV2/5-mAP-3'ABCA4 vectors, or a mix of 1.5 to $5 \times 10^9$ vg of AAV2/5-RK-5'ABCA4-mAP and $5 \times 10^9$ of AAV2/5-mAP-3'ABCA4 vectors in a total volume of 2 μL was administered by subretinal injection into the eyes of Abca4$^{-/-}$ mice.

For RT-qPCR analysis, the neuroretinas were dissected and snap-frozen prior to RNA isolation with RNeasy Mini kit, (Qiagen) and cDNA synthesis was carried out with SuperScript III Reverse Transcriptase (Invitrogen) according to the manufacturer's recommendations. Quantitative PCR analysis was performed using AmpliTaq Gold® 360 Master Mix (Applied Biosystems) and qPCR analysis using Light-Cycler® 480 SYBR Green I Master (Roche).

ABCA4 Gene Transfer in the Rat Retina In Vivo:

Sprague Dawley CD rats were purchased from Charles River and were handled in accordance with the Guide for the Care and Use of Laboratory Animals. For subretinal injections, three months-old rats were anesthetized with 50 mg/kg ketamine and 6 mg/kg xylazine, and an additional local anesthesia was achieved with a drop of oxybuprocaine chlorydrate (1.6 mg/0.4 mL). The pupils were dilated with a drop of 0.5% tropicamide (Mydiatricum, Théa), and subretinal injections were performed under a surgical microscope and controlled by eye fundus examination. Injected eyes were finally covered with Sterdex anti-inflammatory ointment. Animals were injected with either $3.7 \times 10^9$ vg of AAV2/5-RK-5'ABCA4-mAP vector alone, $3.7 \times 10^9$ vg of AAV2/5-mAP-3'ABCA4 vector alone, a mix of $1.85 \times 10^9$ vg of AAV2/5-RK-5'ABCA4-mAP and $1.85 \times 10^9$ vg of AAV2/5-mAP-3'ABCA4 vectors, or a mix of $1.85 \times 10^9$ vg of AAV2/5-CMV-5'ABCA4-mAP and $1.85 \times 10^9$ vg of AAV2/5-mAP-3'ABCA4 vectors, in a total volume of 5 μL.

For RT-qPCR analysis, the neuroretinas were dissected and snap-frozen prior to RNA isolation with NucleoSpin RNA kit (Macherey-Nagel), and cDNA synthesis was carried out with M-MLV Reverse Transcriptase (Invitrogen) according to the manufacturer's recommendations. Quantitative PCR analysis was performed using SYBR qPCR Premix Ex Taq (Takara Bio).

Results

Efficient Production of the Dual AAV2/5-ABCA4 Vectors:

Production of our dual vectors, AAV2/5-CMV-5'ABCA4-mAP and AAV2/5-mAP-3'ABCA4, was effective despite the large size of the vector genomes which are close to the maximum packaging capacity of AAV, that is about 5.1-5.2 kb (Wu et al., Mol Ther 2010). The data (table 1) demonstrated correct production levels (around $10^{13}$ vg per Cell- Stack-5 culture chamber), and a full (vg) to infectious particles ratio—indicative of vector quality—equivalent to that of a standard, regular size, AAV2/5 vector.

TABLE 1

Representative AAV2/5 particles yield obtained with the dual ABCA4 vectors. Total full vector particles (vg) and infectious vector particles (ip) were purified from one transfected CellStack-5 culture chamber and titrated by dot blot hybridization and ICA.

| AAV2/5 vector | total vg | total ip | vg/ip ratio |
|---|---|---|---|
| CMV-5'ABCA4-mAP | $9.1 \times 10^{12}$ | $1.6 \times 10^9$ | $5.8 \times 10^3$ |
| mAP-3'ABCA4-pA | $1.0 \times 10^{13}$ | $1.5 \times 10^9$ | $6.8 \times 10^3$ |

ABCA4 Gene Transfer is Achieved by Infection with the Dual AAV2/5-ABCA4 Vectors In Vitro:

By PCR analysis of DNA extracted from COS-7 cells (FIG. 3), junctions between the 5' and 3' ABCA4 sequences were detected following co-infection with AAV2/5-CMV-5'ABCA4-mAP and AAV2/5-mAP-3'ABCA4 vectors (lanes 9 and 10), or co-transfected with the linearized vector plasmids (lane 6), indicating AP-mediated intermolecular recombination between the vectors and intracellular reconstitution of the full ABCA4 expression cassette, as shown by the presence of a 1.3 kb PCR product. This result was confirmed in other cell lines, e.g. in HEK293. By RT-PCR analysis of RNA extracted from HEK293 cells (FIG. 4), a specific band of 0.3 kb corresponding to spliced ABCA4 mRNA was clearly detected in cells transfected with the control plasmid (lane 5), co-transfected with the linearized 5' and 3' AAV vector plasmids (lane 4), or co-infected with the 5' and 3' AAV2/5 vectors (lane 6). A faint band of the same size was also detected in untreated cells (lane 1) and in cells transfected with a single AAV vector plasmid (lanes 2 and 3), but the signal intensity was much lower. It is possible that the HEK293 cells express low level of ABCA4 mRNA or an mRNA with sequence homology (e.g. encoding another ABC transporter). However, the experiment indicated that AP-mediated intermolecular recombination between the dual vectors actually achieved reconstitution of a full-length, transcriptionally active ABCA4 expression cassette. This result was confirmed in other cell lines, e.g. in HeLa.

By immuno-fluorescence microscopy analysis of HeLa cells (FIG. 5), the PCR and RT-PCR results were confirmed since a specific signal was detected by the anti-ABCA4 3F4 antibody in cells co-infected with the dual AAV2/5-ABCA4 vectors, indicating expression of the ABCA4 protein following intermolecular recombination between the 5' and 3' vector genomes. This result was confirmed in HEK293 cells.

ABCA4 Gene Transfer is Achieved In Vivo by Intramuscular Injection of the Dual AAV2/5-ABCA4 Vectors in the Mouse Skeletal Muscle.

Injection of a mix of AAV2/5-CMV-5'ABCA4-mAP and AAV2/5-mAP-3'ABCA4 vectors was performed into the tibialis anterior muscles of C57/BL6 mice to test ABCA4 gene transfer in vivo in terminally differentiated cells that do not express ABCA4.

PCR analysis of DNA extracted from muscle samples indicated that both the 5'ABCA4 and 3'ABCA4 vector genomes were present within the injected muscle cells, and that junction between both vectors through AP-mediated recombination actually occurred in all four injected muscles (FIG. 6).

RT-PCR analysis of RNA extracted from muscle samples indicated that transcription and splicing of the reconstituted ABCA4 expression cassette also occurred in the injected muscles, as shown by detection of two overlapping fragments spanning the full-length transcript (3.3 kb from the start codon to downstream of the splice acceptor, and 3.8 kb from upstream of the splice donor to the stop codon). Indeed, the 3.3 kb fragment corresponding to the 5' half of ABCA4 mRNA was detected in 3 of the injected muscles, and the 3.8 kb fragment corresponding to the 3' half of ABCA4 mRNA was detected in all 4 injected muscles (FIG. 7).

Immuno-fluorescence microscopy analysis of muscles sections using the 3F4 monoclonal antibody was finally conducted on both non-injected mouse muscles and muscles injected with the dual AAV2/5 vectors (FIG. 8). A specific fluorescent signal was detected only in muscles injected with the AAV vectors. Although the signal was weak and detected only in a few muscle fibers (which could be expected since transduction with AAV5 vectors is poorly efficient in skeletal muscles), this result confirmed that the ABCA4 protein was actually expressed by the dual AAV vectors in vivo.

ABCA4 Gene Transfer is Achieved In Vivo by Subretinal Injection of the Dual AAV2/5-ABCA4 Vectors in the Mouse Eye:

Administration of $2.8 \times 10^9$ vg of AAV2/5-CMV-5'ABCA4-mAP and $2.4 \times 10^9$ vg of AAV2/5-mAP-3'ABCA4 vectors was performed by subretinal injection into the eye of Abca4$^{-/-}$ mice.

Quantitative PCR analysis of reverse transcribed neuroretinal RNA using a F primer situated in exon 21 of the 5' vector and a R primer situated in exon 22 of the 3' vector demonstrated the amplification of a junction fragment specifically in the injected eyes (FIG. 9). No amplification was detected in the eyes from control Abca4+/−(primers specific for the human gene) or Abca4−/− mice. These results indicate that the 5'ABCA4 and 3'ABCA4 vector genomes were present within the injected retina cells, and that junction between both vectors through AP-mediated recombination occurred in all injected eyes. Expression was variable likely due to the difference in the efficiency of detachment per eye. RT-PCR analysis confirmed these results with a fragment of the correct size (183 bp) being detected only in the injected eyes. No amplification was detected in the absence of reverse transcription, excluding the possibility of amplification from a DNA template.

To further confirm that recombination did occur, the qPCR fragments were directly sequenced. Sequence alignment with the ABCA4 coding sequence showed that the amplified product corresponded to the fusion of exon 21-exon 22 following intermolecular recombination and splicing of the intervening alkaline phosphatase-containing intron sequence.

ABCA4 Transgene Expression Following Subretinal Injection of the Dual AAV2/5-ABCA4 Vectors Appears Higher with the RK Promoter Compared to the CMV Promoter, in Both the Mouse and the Rat Eye:

Quantitative PCR analysis of reverse transcribed neuroretinal RNA was performed as described above after subretinal administration of $1.4 \times 10^9$ vg of AAV2/5-CMV-5'ABCA4-mAP or 1.5 to $5 \times 10^9$ vg of AAV2/5-RK-5'ABCA4-mAP vector, together with $1.2 \times 10^9$ vg or $5 \times 10^9$ vg of AAV2/5-mAP-3'ABCA4 into the eye of Abca4$^{-/-}$ mice (FIG. 10). The 183 bp amplification product corresponding to human ABCA4 exon 21-exon 22 junction was detected only in Abca4$^{-/-}$ mice injected with the dual vectors and not in non-injected wild-type (Abca4$^{-/-}$) and Abca4$^{-/-}$ mice. Expression levels of human ABCA4 mRNA in the injected neuroretina were approximately 1.6-fold higher when expressed from the photoreceptor-specific RK promoter as compare to the ubiquitous CMV promoter regardless of dose.

The same quantitative PCR analysis of reverse transcribed neuroretinal RNA was performed after subretinal administration of vectors in Sprague Dawley rats (FIG. 11). Rats were injected with 3.7×10$^9$ vg of AAV2/5-RK-5'ABCA4-mAP vector alone, 3.7×10$^9$ vg of AAV2/5-mAP-3'ABCA4 vector alone, a mix of 1.85×10$^9$ vg of AAV2/5-RK-5'ABCA4-mAP and 1.85×10$^9$ vg of AAV2/5-mAP-3'ABCA4 vectors, or a mix of 1.85×10$^9$ vg of AAV2/5-CMV-5'ABCA4-mAP and 1.85×10$^9$ vg of AAV2/5-mAP-3'ABCA4 vectors. The 183 bp amplification product corresponding to human ABCA4 exon 21-exon 22 junction was detected only in rats injected with the dual vectors, and not in rats injected with either the RK-5'ABCA4-AP or the mAP-3'ABCA4 alone or in non-injected rats. Similarly to the result obtained in the mice, human ABCA4 mRNA expression levels in the rat retinas injected with the dual vectors were found higher (approximately 9.5-fold) when expressed from the photoreceptor-specific RK promoter as compare to the ubiquitous CMV promoter.

REFERENCES

Throughout this application, various references describe the state of the art to which this invention pertains. The disclosures of these references are hereby incorporated by reference into the present disclosure.

Ayuso E, Mingozzi F, Montane J, Leon X, Anguela X M, Haurigot V, Edmonson S A, Africa L, Zhou S, High K A, Bosch F, Wright J F. High AAV vector purity results in serotype- and tissue-independent enhancement of transduction efficiency. Gene Ther. 2010 April; 17(4):503-10.

Ghosh A, Yue Y, Lai Y, Duan D. A hybrid vector system expands adeno-associated viral vector packaging capacity in a transgene-independent manner. Mol Ther. 2008 January; 16(1):124-30.

Grimm D, Kay M A, Kleinschmidt J A. Helper virus-free, optically controllable, and two-plasmid-based production of adeno-associated virus vectors of serotypes 1 to 6. Mol Ther. 2003 June; 7(6):839-50.

Khani S C, Pawlyk B S, Bulgakov O V, Kasperek E, Young J E, Adamian M, Sun X, Smith A J, Ali R R, Li T. AAV-mediated expression targeting of rod and cone photoreceptors with a human rhodopsin kinase promoter. Invest Ophthalmol Vis Sci. 2007 September; 48(9):3954-61.

Salvetti A, Oreve S, Chadeuf G, Favre D, Cherel Y, Champion-Arnaud P, David-Ameline J, Moullier P. Factors influencing recombinant adeno-associated virus production. Hum Gene Ther. 1998 Mar. 20; 9(5):695-706.

Wu Z, Yang H, Colosi P. Effect of genome size on AAV vector packaging. Mol Ther. 2010 January; 18(1):80-6.

The invention claimed is:

1. A hybrid dual rAAV (hdrAAV) vector system suitable for expressing the coding sequence of ABCA4 in a host cell, comprising:
   a) a first rAAV vector containing a first polynucleotide comprising in a 5'-3' direction:
      a 5'-inverted terminal repeat (5'-ITR) sequence;
      a human rhodopsin kinase (RK) promoter sequence;
      the 5' end portion of said coding sequence of ABCA4, said 5' end portion being operably linked to and under control of said promoter;
      the 5' end portion of a sequence of a synthetic intron comprising a nucleic acid sequence of a splicing donor (SD) signal (SEQ ID NO: 1);
      a nucleic acid sequence of a recombinogenic region derived or originating from alkaline phosphatase (AP); and
      a 3'-inverted terminal repeat (3'-ITR) sequence; and
   b) a second rAAV vector containing a second polynucleotide comprising in a 5'-3' direction:
      a 5'-inverted terminal repeat (5'-ITR) sequence;
      a nucleic acid sequence of a recombinogenic region derived or originating from alkaline phosphatase (AP);
      the 3' end portion of a sequence of a synthetic intron comprising a branch site and a polypyrimidine tract (SEQ ID NO: 2);
      a nucleic acid sequence of a splicing acceptor (SA) signal;
      the 3' end of said ABCA4 coding sequence;
      a poly-adenylation signal nucleic acid sequence; and
      a 3'-inverted terminal repeat (3'-ITR) sequence.

2. The hdrAAV vector system of claim 1, wherein the recombinant AAV vectors are selected from the serotype 2, serotype 4, serotype 5 or serotype 8.

3. The hdrAAV vector system of claim 1, wherein the first rAAV vector comprises SEQ ID NO: 13 (AAV-RK-5'ABCA4-mAP vector) and the second rAAV vector comprises SEQ ID NO: 14 (AAV-mAP-SA-3'ABCA4-pA vector).

4. An isolated host cell which has been transduced, transformed or transfected with the hybrid dual viral vector of claim 1.

5. A pharmaceutical composition comprising the hybrid dual viral vector system of claim 1.

6. A pharmaceutical composition comprising the isolated host cell of claim 4 and a pharmaceutically acceptable vehicle.

7. A method of treating a pathology or disease characterized by a retinal degeneration in a subject in need thereof, comprising a step of administering a therapeutically effective amount of the hybrid dual viral vector system according to claim 1 or an isolated host cell comprising said hybrid dual viral vector system.

8. The hdrAAV vector system of claim 1, wherein the recombinogenic region AP comprises SEQ ID NO: 3, SEQ ID No. 4, SEQ ID No. 5, or SEQ ID No. 6.

9. The hdrAAV vector system of claim 1, wherein the 5' end portion of the coding sequence comprises SEQ ID NO: 7 (exons 1-21) and the 3' end of said coding sequence comprises SEQ ID NO: 8 (exons 22-50).

10. The hdrAAV vector system of claim 1, wherein the first polynucleotide comprises SEQ ID NO: 10 (RK-5'ABCA4-SD-AP), and the second polynucleotide comprises SEQ ID NO: 11 (AP-SA-3'ABCA4-pA).

11. The pharmaceutical composition of claim 5, wherein the recombinant AAV vectors are selected from serotype 2, serotype 4, serotype 5 or serotype 8.

12. The pharmaceutical composition of claim 5, wherein the first rAAV vector comprises SEQ ID NO: 13 (AAV-RK-5'ABCA4-mAP vector) and the second rAAV vector comprises SEQ ID NO: 14 (AAV-mAP-SA-3'ABCA4-pA vector).

13. The pharmaceutical composition of claim 5, wherein the recombinogenic region AP comprises SEQ ID NO: 3, SEQ ID No. 4, SEQ ID No. 5, or SEQ ID No. 6.

14. The pharmaceutical composition of claim 5, wherein the 5' end portion of the coding sequence comprises SEQ ID NO: 7 (exons 1-21) and the 3' end of said coding sequence comprises SEQ ID NO: 8 (exons 22-50).

15. The pharmaceutical composition of claim 5, wherein the first polynucleotide comprises SEQ ID NO: 10 (RK-5'ABCA4-SD-AP) and the second polynucleotide comprises SEQ ID NO: 11 (AP-SA-3'ABCA4-pA).

16. The method of claim 7, wherein the recombinant AAV vectors of the hdrAAV vector system are selected from serotype 2, serotype 4, serotype 5 or serotype 8.

17. The method of claim 7, wherein the first rAAV vector comprises SEQ ID NO: 13 (AAV-RK-5' ABCA4-mAP vector), and the second rAAV vector comprises SEQ ID NO: 14 (AAV-mAP-SA-3'ABCA4-pA vector).

18. The method of claim 7, wherein the recombinogenic region AP comprises SEQ ID NO: 3, SEQ ID No. 4, SEQ ID No. 5, or SEQ ID No. 6.

19. The method of claim 7, wherein the 5' end portion of the coding sequence comprises SEQ ID NO: 7 (exons 1-21) and the 3' end of said coding sequence comprises SEQ ID NO: 8 (exons 22-50).

20. The method of claim 7, wherein the first polynucleotide comprises SEQ ID NO: 10 (RK-5'ABCA4-SD-AP) and the second polynucleotide comprises SEQ ID NO: 11 (AP-SA-3' ABCA4-pA).

* * * * *

UNITED STATES PATENT AND TRADEMARK OFFICE
CERTIFICATE OF CORRECTION

PATENT NO. : 11,072,803 B2
APPLICATION NO. : 16/065145
DATED : July 27, 2021
INVENTOR(S) : Vasiliki Kalatzis and Achille Francois It is certified that error appears in the above-identified patent and that said Letters Patent is hereby corrected as shown below:

In the Specification

Column 4,
Line 43, "relates to an to a hybrid" should read --relates to a hybrid--.

Column 10,
Line 39, "COST cells" should read --COS7 cells--.

Column 16,
Line 65, "($Abca4^{-/-}$) and" should read --($Abca4^{+/+}$) and--.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 14

<210> SEQ ID NO 1
<211> LENGTH: 28
<212> TYPE: DNA
<213> ORGANISM: Artificial
<220> FEATURE:
<223> OTHER INFORMATION: Splicing donor signal

<400> SEQUENCE: 1
gtaagtatca aggttacaag acaggttt                                          28

<210> SEQ ID NO 2
<211> LENGTH: 105
<212> TYPE: DNA
<213> ORGANISM: Artificial
<220> FEATURE:
<223> OTHER INFORMATION: Branch site, polypyrimidine tract and splicing
      acceptor signal

<400> SEQUENCE: 2
aaggagacca atagaaactg ggcttgtcga gacagagaag actcttgcgt ttctgatagg        60
cacctattgg tcttactgac atccactttg cctttctctc cacag                       105

<210> SEQ ID NO 3
<211> LENGTH: 887
<212> TYPE: DNA
<213> ORGANISM: Artificial
<220> FEATURE:
<223> OTHER INFORMATION: Recombinogenic AP sequence

<400> SEQUENCE: 3
gtgatcctag gtggaggccg aaagtacatg tttcgcatgg gaaccccaga ccctgagtac        60
ccagatgact acagccaagg tgggaccagg ctggacggga agaatctggt gcaggaatgg       120
ctcggcgaac gccagggtgc ccggtacgtg tggaaccgca ctgagctcat gcaggcttcc       180
```

```
ctggacccgt ctgtgaccca tctcatgggt ctctttgagc ctggagacat gaaatacgag    240
atccaccgag actccacact ggacccctcc ctgatggaga tgacagaggc tgccctgcgc    300
ctgctgagca gacaccccg cggcttcttc ctcttcgtgg agggtggtcg catcgaccat    360
ggtcatcatg aaagcagggc ttaccgggca ctgactgaga cgatcatgtt cgacgacgcc    420
attgagaggg cgggccagct caccagcgag gaggacacgc tgagcctcgt cactgccgac    480
cactcccacg tcttctcctt cggaggctac cccctgcgag ggagctcctt catcgggctg    540
gccgctggca aggcccggga caggaaggcc tacacggtcc tcctatacgg aaacggtcca    600
ggctatgtgc tcaaggacgg cgcccggccg gatgttaccg agagcgagag cgggagcccc    660
gagtatcggc agcagtcagc agtgcccctg gacgaagaga cccacgcagg cgaggacgtg    720
gcggtgttcg cgcgcggccc gcaggcgcac ctggttcacg gcgtgcagga gcagaccttc    780
atagcgcacg tcatggcctt cgccgcctgc ctggagccct acaccgcctg cgacctggcg    840
ccccccgccg gcaccaccga cgccgcgcac ccggggcggt ccgtggt              887

<210> SEQ ID NO 4
<211> LENGTH: 286
<212> TYPE: DNA
<213> ORGANISM: Artificial
<220> FEATURE:
<223> OTHER INFORMATION: Recombinogenic AP 1/3 head sequence

<400> SEQUENCE: 4
tggaggccga aagtacatgt ttcgcatggg aacccccagac cctgagtacc cagatgacta     60
cagccaaggt gggaccaggc tggacgggaa gaatctggtg caggaatggc tcggcgaacg    120
ccagggtgcc cggtacgtgt ggaaccgcac tgagctcatg caggcttccc tggacccgtc    180
tgtgacccat ctcatgggtc tctttgagcc tggagacatg aaatacgaga tccaccgaga    240
ctccacactg gaccctccc tgatggagat gacagaggct gccctg                    286

<210> SEQ ID NO 5
<211> LENGTH: 287
<212> TYPE: DNA
<213> ORGANISM: Artificial
<220> FEATURE:
<223> OTHER INFORMATION: Recombinogenic AP 1/3 tail sequence

<400> SEQUENCE: 5
gaaacggtcc aggctatgtg ctcaaggacg gcgcccggcc ggatgttacc gagagcgaga     60
gcgggagccc cgagtatcgg cagcagtcag cagtgcccct ggacgaagag acccacgcag    120
gcgaggacgt ggcggtgttc gcgcgcggcc cgcaggcgca cctggttcac ggcgtgcagg    180
agcagacctt catagcgcac gtcatggcct tcgccgcctg cctggagccc tacaccgcct    240
gcgacctggc gccccccgcc ggcaccaccg acgccgcgca cccgggg              287

<210> SEQ ID NO 6
<211> LENGTH: 877
<212> TYPE: DNA
<213> ORGANISM: Artificial
<220> FEATURE:
<223> OTHER INFORMATION: Recombinogenic mAP sequence

<400> SEQUENCE: 6
cctaggtgga ggccgaaagt acaagtttcg ctagggaacc ccagaccctg agtacccagt     60
agactacagc caaggtggga ccaggctgga cgggaagaat ctggtgcagg ataggctcgg    120
```

| | |
|---|---|
| cgaacgccag ggtgcccggt acgtgtggaa ccgcactgag gtctagcagg cttccctgga | 180 |
| cccgtctgtg accctactct agggtctctt tgagcctgga gactagaaat acgagatcca | 240 |
| ccgagactcc acactggacc cctccctgta ggagtagaca gaggctgccc tgcgcctgct | 300 |
| gagcagacac ccgcgcggct tcttcctctt cgtggagggt ggtcgctacg accaaggtca | 360 |
| tcttgaaagc agggcttacc gggcactgac tgagacgatc tagttcgacg acgccttgag | 420 |
| agggcgggcc agctcaccag cgaggaggac acgctgagcc tcgtcactgc cgaccactcc | 480 |
| cacgtcttct ccttcggagg ctaccccctg cgagggaggt ccttcaacgg gctggccgct | 540 |
| ggcaaggccc gggacaggaa ggcctacacg gtcctcctat acggaaacgg tccaggctta | 600 |
| gtgctcaagg acggcgcccg gccggtagtt accgagagcg agagcgggag ccccgagtat | 660 |
| cggcagcagt cagcagtgcc cctgacgaa gagacccacg caggcgagga cgtggcggtg | 720 |
| ttcgcgcgcg gcccgcaggc gcacctggtt cacggcgtgc aggagcagac cttctaagcg | 780 |
| cacgtctagg ccttcgccgc ctgcctggag ccctacaccg cctgcgacct ggcgcccccc | 840 |
| gccggcacca ccgacgccgc gcacccgggg cggtccg | 877 |

<210> SEQ ID NO 7
<211> LENGTH: 3190
<212> TYPE: DNA
<213> ORGANISM: Artificial
<220> FEATURE:
<223> OTHER INFORMATION: ABCA4 exons 1-21 coding sequence

<400> SEQUENCE: 7

| | |
|---|---|
| atgggcttcg tgagacagat acagcttttg ctctggaaga actggaccct gcggaaaagg | 60 |
| caaaagattc gctttgtggt ggaactcgtg tggcctttat ctttatttct ggtcttgatc | 120 |
| tggttaagga atgccaaccc gctctacagc catcatgaat gccatttccc caacaaggcg | 180 |
| atgccctcag caggaatgct gccgtggctc caggggatct tctgcaatgt gaacaatccc | 240 |
| tgttttcaaa gccccacccc aggagaatct cctggaattg tgtcaaacta taacaactcc | 300 |
| atcttggcaa gggtatatcg agattttcaa gaactcctca tgaatgcacc agagagccag | 360 |
| caccttggcc gtatttggac agagctacac atcttgtccc aattcatgga caccctccgg | 420 |
| actcacccgg agagaattgc aggaagagga atacgaataa gggatatctt gaaagatgaa | 480 |
| gaaacactga cactatttct cattaaaaac atcggcctgt ctgactcagt ggtctacctt | 540 |
| ctgatcaact ctcaagtccg tccagagcag ttcgctcatg gagtcccgga cctggcgctg | 600 |
| aaggacatcg cctgcagcga ggccctcctg gagcgcttca tcatcttcag ccagagacgc | 660 |
| ggggcaaaga cggtgcgcta tgccctgtgc tccctctccc agggcaccct acagtggata | 720 |
| gaagacactc tgtatgccaa cgtggacttc ttcaagctct ccgtgtgct ccacacactc | 780 |
| ctagacagcc gttctcaagg tatcaatctg agatcttggg aggaatatt atctgatatg | 840 |
| tcaccaagaa ttcaagagtt tatccatcgg ccgagtatgc aggacttgct gtgggtgacc | 900 |
| aggcccctca tgcagaatgg tggtccagag acctttacaa agctgatggg catcctgtct | 960 |
| gacctcctgt gtggctaccc cgagggaggt ggctctcggg tgctctcctt caactggtat | 1020 |
| gaagacaata actataaggc ctttctgggg attgactcca caaggaagga tcctatctat | 1080 |
| tcttatgaca gaagaacaac atccttttgt aatgcattga tccagagcct ggagtcaaat | 1140 |
| cctttaacca aaatcgcttg gagggcggca aagcctttgc tgatgggaaa aatcctgtac | 1200 |
| actcctgatt cacctgcagc acgaaggata ctgaagaatg ccaactcaac ttttgaagaa | 1260 |
| ctggaacacg ttaggaagtt ggtcaaagcc tgggaagaag tagggcccca gatctggtac | 1320 |

```
ttctttgaca acagcacaca gatgaacatg atcagagata ccctgggaa cccaacagta    1380 aaagactttt tgaataggca gcttggtgaa aaggtatta ctgctgaagc catcctaaac    1440
ttcctctaca agggccctcg ggaaagccag gctgacgaca tggccaactt cgactggagg    1500
gacatattta acatcactga tcgcaccctc cgcctggtca atcaatacct ggagtgcttg    1560
gtcctggata agtttgaaag ctacaatgat gaaactcagc tcacccaacg tgccctctct    1620
ctactggagg aaaacatgtt ctgggccgga gtggtattcc ctgacatgta tcctggacc     1680 agctctctac caccccacgt gaagtataag atccgaatgg acatagacgt ggtggagaaa    1740
accaataaga ttaaagacag gtattgggat tctggtccca gagctgatcc cgtggaagat    1800
ttccggtaca tctggggcgg gtttgcctat ctgcaggaca tggttgaaca ggggatcaca    1860
aggagccagg tgcaggcgga ggctccagtt ggaatctacc tccagcagat gccctacccc    1920
tgcttcgtgg acgattcttt catgatcatc ctgaaccgct gtttccctat cttcatggtg    1980
ctggcatgga tctactctgt ctccatgact gtgaagagca tcgtcttgga aaggagttg    2040 cgactgaagg agaccttgaa aaatcagggt gtctccaatg cagtgatttg gtgtacctgg    2100
ttcctggaca gcttctccat catgtcgatg agcatcttcc tcctgacgat attcatcatg    2160
catggaagaa tcctacatta cagcgaccca ttcatcctct tcctgttctt gttggctttc    2220
tccactgcca ccatcatgct gtgctttctg ctcagcacct tcttctccaa ggccagtctg    2280
gcagcagcct gtagtggtgt catctattc accctctacc tgccacacat cctgtgcttc    2340
gcctggcagg accgcatgac cgctgagctg aagaaggctg tgagcttact gtctccggtg    2400
gcatttggat ttggcactga gtacctggtt cgctttgaag agcaaggcct ggggctgcag    2460
tggagcaaca tcgggaacag tcccacggaa ggggacgaat tcagcttcct gctgtccatg    2520
cagatgatgc tccttgatgc tgctgtctat ggcttactcg cttggtacct tgatcaggtg    2580
tttccaggag actatggaac cccacttcct tggtactttc ttctacaaga gtcgtattgg    2640
cttggcggtg aagggtgttc aaccagagaa gaaagagccc tggaaaagac cgagccccta    2700
acagaggaaa cggaggatcc agagcaccca gaaggaatac acgactcctt ctttgaacgt    2760
gagcatccag ggtgggttcc tggggtatgc gtgaagaatc tggtaaagat ttttgagccc    2820
tgtggccggc cagctgtgga ccgtctgaac atcaccttct acgagaacca gatcaccgca    2880
ttcctgggcc acaatggagc tgggaaaacc accaccttgt ccatcctgac gggtctgttg    2940
ccaccaacct ctgggactgt gctcgttggg ggaagggaca ttgaaaccag cctggatgca    3000
gtccggcaga gccttggcat gtgtccacag cacaacatcc tgttccacca cctcacggtg    3060
gctgagcaca tgctgttcta tgcccagctg aaaggaaagt cccaggagga ggcccagctg    3120
gagatggaag ccatgttgga ggacacaggc ctccaccaca agcggaatga agaggctcag    3180
gacctatcag                                                          3190

<210> SEQ ID NO 8
<211> LENGTH: 3632
<212> TYPE: DNA
<213> ORGANISM: Artificial
<220> FEATURE:
<223> OTHER INFORMATION: ABCA4 exons 22-50 coding sequence

<400> SEQUENCE: 8
gtggcatgca gagaaagctg tcggttgcca ttgcctttgt gggagatgcc aaggtggtga      60
ttctggacga acccacctct ggggtggacc cttactcgag acgctcaatc tgggatctgc     120
```

-continued

```
tcctgaagta tcgctcaggc agaaccatca tcatgtccac tcaccacatg gacgaggccg    180
acctccttgg ggaccgcatt gccatcattg cccagggaag gctctactgc tcaggcaccc    240
cactcttcct gaagaactgc tttggcacag gcttgtactt aaccttggtg cgcaagatga    300
aaaacatcca gagccaaagg aaaggcagtg aggggacctg cagctgctcg tctaagggtt    360
tctccaccac gtgtccagcc cacgtcgatg acctaactcc agaacaagtc ctggatgggg    420
atgtaaatga gctgatggat gtagttctcc accatgttcc agaggcaaag ctggtggagt    480
gcattggtca agaacttatc ttccttcttc caaataagaa cttcaagcac agagcatatg    540 ccagccttt cagagagctg gaggagacgc tggctgacct tggtctcagc agttttggaa    600
tttctgacac tccctggaa gagattttc tgaaggtcac ggaggattct gattcaggac    660
ctctgtttgc gggtggcgct cagcagaaaa gagaaacgt caaccccga caccctgct    720 tgggtcccag agaaaggct ggacagacac cccaggactc caatgtctgc tccccagggg    780
cgccggctgc tcacccagag gccagcctc cccagagcc agagtgccca ggcccgcagc    840
tcaacacggg gacacagctg gtcctccagc atgtgcaggc gctgctggtc aagagattcc    900
aacacaccat ccgcagccac aaggacttcc tggcgcagat cgtgctcccg gctaccttg    960 tgtttttggc tctgatgctt tctattgtta ccctccttt tggcgaatac cccgctttga    1020
cccttcaccc ctggatatat gggcagcagt acaccttctt cagcatggat gaaccaggca    1080
gtgagcagtt cacggtactt gcagacgtcc tcctgaataa gccaggcttt ggcaaccgct    1140
gcctgaagga agggtggctt ccggagtacc cctgtggcaa ctcaacaccc tggaagactc    1200
cttctgtgtc cccaaacatc acccagctgt tccagaagca gaaatggaca caggtcaacc    1260
cttcaccatc ctgcaggtgc agcaccaggg agaagctcac catgctgcca gagtgccccg    1320
agggtgccgg gggcctcccg ccccccagaa gaacacagcg cagcacggaa attctacaag    1380
acctgacgga caggaacatc tccgacttct tggtaaaaac gtatcctgct cttataagaa    1440
gcagcttaaa gagcaaattc tgggtcaatg aacagaggta tggaggaatt tccattggag    1500
gaaagctccc agtcgtcccc atcacggggg aagcacttgt tgggtttta agcgaccttg    1560 gccggatcat gaatgtgagc gggggcccta tcactagaga ggcctctaaa gaaatacctg    1620
atttccttaa acatctagaa actgaagaca acattaaggt gtggtttaat aacaaaggct    1680
ggcatgccct ggtcagcttt ctcaatgtgg cccacaacgc catcttacgg gccagcctgc    1740
ctaaggacag gagccccgag gagtatggaa tcaccgtcat tagccaaccc ctgaacctga    1800
ccaaggagca gctctcagag attacagtgc tgaccacttc agtggatgct gtggttgcca    1860
tctgcgtgat tttctccatg tccttcgtcc cagccagctt tgtcctttat ttgatccagg    1920
agcgggtgaa caaatccaag cacctccagt ttatcagtgg agtgagcccc accacctact    1980
gggtgaccaa cttcctctgg gacatcatga attattccgt gagtgctggg ctggtggtgg    2040
gcatcttcat cgggttttcag aagaaagcct acacttctcc agaaaaccctt cctgcccttg    2100 tggcactgct cctgctgtat ggatgggcgg tcattcccat gatgtaccca gcatccttcc    2160
tgtttgatgt ccccagcaca gcctatgtgg ctttatcttg tgctaatctg ttcatcggca    2220
tcaacagcag tgctattacc ttcatcttgg aattatttga gaataaccgg acgctgctca    2280
ggttcaacgc cgtgctgagg aagctgctca ttgtcttccc ccacttctgc ctgggccggg    2340
gcctcattga cctgcactg agccaggctg tgacagatgt ctatgccgg tttggtgagg    2400 agcactctgc aaatccgttc cactgggacc tgattgggaa gaacctgttt gccatggtgg    2460
tggaaggggt ggtgtacttc ctcctgaccc tgctggtcca gcgccacttc ttcctctccc    2520
```

| | | |
|---|---|---|
| aatggattgc cgagcccact aaggagccca ttgttgatga agatgatgat gtggctgaag | 2580 | |
| aaagacaaag aattattact ggtggaaata aaactgacat cttaaggcta catgaactaa | 2640 | |
| ccaagattta tccaggcacc tccagcccag cagtggacag gctgtgtgtc ggagttcgcc | 2700 | |
| ctggagagtg ctttggcctc ctgggagtga atggtgccgg caaaacaacc acattcaaga | 2760 | |
| tgctcactgg ggacaccaca gtgacctcag gggatgccac cgtagcaggc aagagtattt | 2820 | |
| taaccaatat ttctgaagtc catcaaaata tgggctactg tcctcagttt gatgcaattg | 2880 | |
| atgagctgct cacaggacga gaacatcttt acctttatgc ccggcttcga ggtgtaccag | 2940 | |
| cagaagaaat cgaaaaggtt gcaaactgga gtattaagag cctgggcctg actgtctacg | 3000 | |
| ccgactgcct ggctggcacg tacagtgggg gcaacaagcg gaaactctcc acagccatcg | 3060 | |
| cactcattgg ctgcccaccg ctggtgctgc tggatgagcc caccacaggg atggaccccc | 3120 | |
| aggcacgccg catgctgtgg aacgtcatcg tgagcatcat cagagaaggg agggctgtgg | 3180 | |
| tcctcacatc ccacagcatg gaagaatgtg aggcactgtg tacccggctg gccatcatgg | 3240 | |
| taaagggcgc ctttcgatgt atgggcacca ttcagcatct caagtccaaa tttggagatg | 3300 | |
| gctatatcgt cacaatgaag atcaaatccc gaaggacga cctgcttcct gacctgaacc | 3360 | |
| ctgtggagca gttcttccag gggaacttcc caggcagtgt gcagagggag aggcactaca | 3420 | |
| acatgctcca gttccaggtc tcctcctcct ccctggcgag gatcttccag ctcctcctct | 3480 | |
| cccacaagga cagcctgctc atcgaggagt actcagtcac acagaccaca ctggaccagg | 3540 | |
| tgtttgtaaa ttttgctaaa cagcagactg aaagtcatga cctccctctg caccctcgag | 3600 | |
| ctgctggagc cagtcgacaa gcccaggact ga | 3632 | |

<210> SEQ ID NO 9
<211> LENGTH: 4774
<212> TYPE: DNA
<213> ORGANISM: Artificial
<220> FEATURE:
<223> OTHER INFORMATION: CMV-5'ABCA4-SD-mAP cassette

<400> SEQUENCE: 9

| | | |
|---|---|---|
| ctagttatta atagtaatca attacggggt cattagttca tagcccatat atggagttcc | 60 | |
| gcgttacata acttacggta aatggcccgc ctggctgacc gcccaacgac ccccgcccat | 120 | |
| tgacgtcaat aatgacgtat gttcccatag taacgccaat agggactttc cattgacgtc | 180 | |
| aatgggtgga gtatttacgg taaactgccc acttggcagt acatcaagtg tatcatatgc | 240 | |
| caagtacgcc ccctattgac gtcaatgacg gtaaatggcc cgcctggcat tatgcccagt | 300 | |
| acatgacctt atgggacttt cctacttggc agtacatcta cgtattagtc atcgctatta | 360 | |
| ccatggtgat gcggttttgg cagtacatca atgggcgtgg atagcggttt gactcacggg | 420 | |
| gatttccaag tctccacccc attgacgtca atgggagttt gttttggcac caaaatcaac | 480 | |
| gggactttcc aaaatgtcgt aacaactccg ccccattgac gcaaatgggc ggtaggcgtg | 540 | |
| tacggtggga ggtctatata agcagagctc tctggctaac tagagaaccc actgcttact | 600 | |
| ggcttatcga aattaatacg actcactata gggagaccca gctggctag actcgagaag | 660 | |
| ctttaaagcc accatgggct tcgtgagaca gatacagctt ttgctctgga gaactggac | 720 | |
| cctgcggaaa aggcaaaaga ttcgctttgt ggtggaactc gtgtggcctt atctttatt | 780 | |
| tctggtcttg atctggttaa ggaatgccaa cccgctctac agccatcatg aatgccattt | 840 | |
| ccccaacaag gcgatgccct cagcaggaat gctgccgtgg ctccagggga tcttctgcaa | 900 | |

-continued

```
tgtgaacaat ccctgttttc aaagccccac cccaggagaa tctcctggaa ttgtgtcaaa    960
ctataacaac tccatcttgg caagggtata tcgagatttt caagaactcc tcatgaatgc   1020
accagagagc cagcaccttg gccgtatttg acagagcta cacatcttgt cccaattcat    1080
ggacaccctc cggactcacc cggagagaat tgcaggaaga ggaatacgaa taagggatat   1140
cttgaaagat gaagaaacac tgacactatt tctcattaaa aacatcggcc tgtctgactc   1200
agtggtctac cttctgatca actctcaagt ccgtccagag cagttcgctc atggagtccc   1260
ggacctggcg ctgaaggaca tcgcctgcag cgaggccctc ctggagcgct tcatcatctt   1320
cagccagaga cgcggggcaa agacggtgcg ctatgccctg tgctccctct cccagggcac   1380
cctacagtgg atagaagaca ctctgtatgc caacgtggac ttcttcaagc tcttccgtgt   1440
gcttcccaca ctcctagaca gccgttctca aggtatcaat ctgagatctt ggggaggaat   1500
attatctgat atgtcaccaa gaattcaaga gtttatccat cggccgagta tgcaggactt   1560
gctgtgggtg accaggcccc tcatgcagaa tggtggtcca gagaccttta caaagctgat   1620
gggcatcctg tctgacctcc tgtgtggcta ccccgaggga ggtggctctc gggtgctctc   1680
cttcaactgg tatgaagaca ataactataa ggcctttctg gggattgact ccacaaggaa   1740
ggatcctatc tattcttatg acagaagaac aacatccttt tgtaatgcat tgatccagag   1800
cctggagtca aatcctttaa ccaaaatcgc ttggagggcg gcaaagcctt tgctgatggg   1860
aaaaatcctg tacactcctg attcacctgc agcacgaagg atactgaaga atgccaactc   1920
aactttgaa gaactggaac acgttaggaa gttggtcaaa gcctgggaag aagtagggcc    1980
ccagatctgt tacttctttg acaacagcac acagatgaac atgatcagag atacccctggg  2040
gaacccaaca gtaaaagact ttttgaatag gcagcttggt gaagaaggta ttactgctga   2100
agccatccta aacttcctct acaagggccc tcgggaaagc caggctgacg acatggccaa   2160
cttcgactgg agggacatat ttaacatcac tgatcgcacc ctccgcctgg tcaatcaata   2220
cctggagtgc ttggtcctgg ataagtttga aagctacaat gatgaaactc agctcaccca   2280
acgtgccctc tctctactgg aggaaaacat gttctgggcc ggagtggtat ccctgacat    2340
gtatccctgg accagctctc taccacccca cgtgaagtat aagatccgaa tggacataga   2400
cgtggtggag aaaaccaata agattaaaga caggtattgg gattctggtc ccagagctga   2460
tcccgtggaa gatttccggt acatctgggg cgggttgcc tatctgcagg acatggttga    2520
acaggggatc acaaggagcc aggtgcaggc ggaggctcca gttggaatct acctccagca   2580
gatgccctac ccctgcttcg tggacgattc tttcatgatc atcctgaacc gctgtttccc   2640
tatcttcatg gtgctggcat ggatctactc tgtctccatg actgtgaaga gcatcgtctt   2700
ggagaaggag ttgcgactga aggagacctt gaaaaatcag ggtgtctcca atgcagtgat   2760
ttggtgtacc tggttcctgg acagcttctc catcatgtcg atgagcatct tcctcctgac   2820
gatattcatc atgcatggaa gaatcctaca ttacagcgac ccattcatcc tcttcctgtt   2880
cttgttggct ttctccactg ccaccatcat gctgtgcttt ctgctcagca ccttcttctc   2940
caaggccagt ctggcagcag cctgtagtgg tgtcatctat ttcaccctct acctgccaca   3000
catcctgtgc ttcgcctggc aggaccgcat gaccgctgag ctgaagaagg ctgtgagctt   3060
actgtctccg gtggcatttg gatttggcac tgagtacctg gttcgctttg aagagcaagg   3120
cctggggctg cagtggagca acatcgggaa cagtcccacg gaaggggacg aattcagctt   3180
cctgctgtcc atgcagatga tgctccttga tgctgctgtc tatggcttac tcgcttggta   3240
ccttgatcag gtgtttccag gagactatgg aaccccactt ccttggtact tcttctacta   3300
```

```
agagtcgtat tggcttggcg gtgaagggtg ttcaaccaga gaagaaagag ccctggaaaa   3360
gaccgagccc ctaacagagg aaacggagga tccagagcac ccagaaggaa tacacgactc   3420
cttctttgaa cgtgagcatc cagggtgggt tcctggggta tgcgtgaaga atctggtaaa   3480
gatttttgag ccctgtggcc ggccagctgt ggaccgtctg aacatcacct tctacgagaa   3540
ccagatcacc gcattcctgg ccacaatgg agctgggaaa accaccacct tgtccatcct   3600
gacgggtctg ttgccaccaa cctctgggac tgtgctcgtt ggggaaggg acattgaaac   3660
cagcctggat gcagtccggc agagccttgg catgtgtcca cagcacaaca tcctgttcca   3720
ccacctcacg gtggctgagc acatgctgtt ctatgcccag ctgaaaggaa gtcccagga   3780
ggaggcccag ctggagatgg aagccatgtt ggaggacaca ggcctccacc acaagcggaa   3840
tgaagaggct caggacctat caggtaagta tcaaggttac aagacaggtt ccgcggcct   3900
aggtggaggc cgaaagtaca gtttcgcta gggaaccca gaccctgagt acccagtaga   3960
ctacagccaa ggtgggacca ggctggacgg gaagaatctg tgcaggata ggctcggcga   4020
acgccagggt gcccggtacg tgtggaaccg cactgaggtc tagcaggctt ccctggaccc   4080
gtctgtgacc ctactctagg gtctctttga gcctggagac tagaaatacg agatccaccg   4140
agactccaca ctggacccct ccctgtagga gtagacagag gctgccctgc cctgctgag   4200
cagacacccg cgcggcttct tcctcttcgt ggagggtggt cgctacgacc aaggtcatct   4260
tgaaagcagg gcttaccggg cactgactga gacgatctag ttcgacgacg ccttgagagg   4320
gcggggccagc tcaccagcga ggaggacacg ctgagcctcg tcactgccga ccactcccac   4380
gtcttctcct tcggaggcta cccctgcga gggaggtcct tcaacgggct ggccgctggc   4440
aaggcccggg acaggaaggc ctacacggtc ctcctatacg gaaacggtcc aggcttagtg   4500
ctcaaggacg gcgcccggcc ggtagttacc gagagcgaga gcgggagccc cgagtatcgg   4560
cagcagtcag cagtgcccct ggacgaagag acccacgcag gcgaggacgt ggcggtgttc   4620
gcgcgcggcc cgcaggcgca cctggttcac ggcgtgcagg agcagacctt ctaagcgcac   4680
gtctaggcct tcgccgcctg cctggagccc tacaccgcct gcgacctggc gccccccgcc   4740
ggcaccaccg acgccgcgca cccggggcgg tccg                              4774
```

<210> SEQ ID NO 10
<211> LENGTH: 4321
<212> TYPE: DNA
<213> ORGANISM: Artificial
<220> FEATURE:
<223> OTHER INFORMATION: RK-5'ABCA4-SD-mAP cassette

<400> SEQUENCE: 10

```
gggcccaga agcctggtgg ttgtttgtcc ttctcagggg aaaagtgagg cggcccttg      60
gaggaagggg ccgggcagaa tgatctaatc ggattccaag cagctcaggg gattgtcttt    120
ttctagcacc ttcttgccac tcctaagcgt cctccgtgac cccggctggg atttagcctg    180
gtgctgtgtc agccccgggt cgacaagctt taaagccacc atgggcttcg tgagacagat    240
acagcttttg ctctggaaga actgaccct gcggaaaagg caaagagattc gctttgtggt    300
ggaactcgtg tggcctttat ctttatttct ggtcttgatc tggttaagga atgccaaccc    360
gctctacagc catcatgaat gccatttccc caacaaggcg atgccctcag caggaatgct    420
gccgtggctc caggggatct tctgcaatgt gaacaatccc tgttttcaaa gccccacccc    480
aggagaatct cctggaattg tgtcaaacta taacaactcc atcttggcaa gggtatatcg    540
```

| | | |
|---|---|---|
| agattttcaa gaactcctca tgaatgcacc agagagccag caccttggcc gtatttggac | 600 |
| agagctacac atcttgtccc aattcatgga caccctccgg actcacccgg agagaattgc | 660 |
| aggaagagga atacgaataa gggatatctt gaaagatgaa gaaacactga cactatttct | 720 |
| cattaaaaac atcggcctgt ctgactcagt ggtctacctt ctgatcaact ctcaagtccg | 780 |
| tccagagcag ttcgctcatg gagtcccgga cctggcgctg aaggacatcg cctgcagcga | 840 |
| ggccctcctg gagcgcttca tcatcttcag ccagagacgc ggggcaaaga cggtgcgcta | 900 |
| tgccctgtgc tccctctccc agggcaccct acagtggata aagacactc tgtatgccaa | 960 |
| cgtggacttc ttcaagctct ccgtgtgct cccacactc ctagacagcc gttctcaagg | 1020 |
| tatcaatctg agatcttggg gaggaatatt atctgatatg tcaccaagaa ttcaagagtt | 1080 |
| tatccatcgg ccgagtatgc aggacttgct gtgggtgacc aggcccctca tgcagaatgg | 1140 |
| tggtccagag acctttacaa agctgatggg catcctgtct gacctcctgt gtggctaccc | 1200 |
| cgagggaggt ggctctcggg tgctctcctt caactggtat gaagacaata actataaggc | 1260 |
| cttttctgggg attgactcca caaggaagga tcctatctat tcttatgaca gaagaacaac | 1320 |
| atccttttgt aatgcattga tccagagcct ggagtcaaat cctttaacca aaatcgcttg | 1380 |
| gagggcggca aagcctttgc tgatgggaaa atcctgtac actcctgatt cacctgcagc | 1440 |
| acgaaggata ctgaagaatg ccaactcaac ttttgaagaa ctggaacacg ttaggaagtt | 1500 |
| ggtcaaagcc tggaagaag tagggccca gatctgtac ttctttgaca cagcacaca | 1560 |
| gatgaacatg atcagagata ccctggggaa cccaacagta aaagacttt tgaataggca | 1620 |
| gcttggtgaa gaaggtatta ctgctgaagc catcctaaac ttcctctaca agggccctcg | 1680 |
| ggaaagccag gctgacgaca tggccaactt cgactggagg gacatatttta acatcactga | 1740 |
| tcgcaccctc cgcctggtca atcaataccct ggagtgcttg gtcctggata agtttgaaag | 1800 |
| ctacaatgat gaaactcagc tcacccaacg tgccctctct ctactggagg aaaacatgtt | 1860 |
| ctgggccgga gtggtattcc ctgacatgta ccctggacc agctctctac caccccacgt | 1920 |
| gaagtataag atccgaatgg acatagacgt ggtggagaaa accaataaga ttaaagacag | 1980 |
| gtattgggat tctggtccca gagctgatcc cgtggaagat ttccggtaca tctgggggcgg | 2040 |
| gtttgcctat ctgcaggaca tggttgaaca ggggatcaca aggagccagg tgcaggcgga | 2100 |
| ggctccagtt ggaatctacc tccagcagat gccctacccc tgcttcgtgg acgattcttt | 2160 |
| catgatcatc ctgaaccgct gtttccctat cttcatggtg ctggcatgga tctactctgt | 2220 |
| ctccatgact gtgaagagca tcgtcttgga gaaggagttg cgactgaagg agaccttgaa | 2280 |
| aaatcagggt gtctccaatg cagtgatttg gtgtacctgg ttcctggaca gcttctccat | 2340 |
| catgtcgatg agcatcttcc tcctgacgat attcatcatg catggaagaa tcctacatta | 2400 |
| cagcgaccca ttcatcctct cctgttcctt gttggctttc tccactgcca ccatcatgct | 2460 |
| gtgctttctg ctcagcacct tcttctccaa ggccagtctg gcagcagcct gtagtggtgt | 2520 |
| catctatttc accctctacc tgccacacat cctgtgcttc gcctggcagg accgcatgac | 2580 |
| cgctgagctg aagaaggctg tgagcttact gtctccggtg gcatttggat ttggcactga | 2640 |
| gtacctggtt cgctttgaag agcaaggcct ggggctgcag tggagcaaca tcgggaacag | 2700 |
| tcccacggaa ggggacgaat tcagcttcct gctgtccatg cagatgatgc tccttgatgc | 2760 |
| tgctgtctat ggcttactcg cttggtacct tgatcaggtg tttccaggag actatggaac | 2820 |
| cccacttcct tggtactttc ttctacaaga gtcgtattgg cttggcggtg aagggtgttc | 2880 |
| aaccagagaa gaaagagccc tggaaaagac cgagcccta acagaggaaa cggaggatcc | 2940 |

```
agagcaccca gaaggaatac acgactcctt ctttgaacgt gagcatccag ggtgggttcc    3000
tggggtatgc gtgaagaatc tggtaaagat ttttgagccc tgtggccggc cagctgtgga    3060
ccgtctgaac atcaccttct acgagaacca gatcaccgca ttcctgggcc acaatggagc    3120
tgggaaaacc accaccttgt ccatcctgac gggtctgttg ccaccaacct ctgggactgt    3180
gctcgttggg ggaagggaca ttgaaaccag cctggatgca gtccggcaga gccttggcat    3240
gtgtccacag cacaacatcc tgttccacca cctcacggtg gctgagcaca tgctgttcta    3300
tgcccagctg aaaggaaagt cccaggagga ggcccagctg agatggaag ccatgttgga     3360 ggacacaggc ctccaccaca agcggaatga agaggctcag gacctatcag gtaagtatca    3420
aggttacaag acaggtttcc gcggcctagg tgaggccga aagtacaagt tcgctaggg      3480 aaccccagac cctgagtacc cagtagacta cagccaaggt gggaccaggc tggacgggaa    3540
gaatctggtg caggataggc tcggcgaacg ccagggtgcc cggtacgtgt ggaaccgcac    3600
tgaggtctag caggcttccc tggacccgtc tgtgaccta ctctagggtc tctttgagcc     3660
tggagactag aaatacgaga tccaccgaga ctccacactg gacccctccc tgtaggagta    3720
gacagaggct gccctgcgcc tgctgagcag acacccgcgc ggcttcttcc tcttcgtgga    3780
gggtggtcgc tacgaccaag gtcatcttga aagcagggct taccgggcac tgactgagac    3840
gatctagttc gacgacgcct tgagagggcg ggccagctca ccagcgagga ggacacgctg    3900
agcctcgtca ctgccgacca ctcccacgtc ttctccttcg gaggctaccc cctgcgaggg    3960
aggtccttca acgggctggc cgctggcaag gcccgggaca ggaaggccta cacggtcctc    4020
ctatacggaa acggtccagg cttagtgctc aaggacggcg cccggccggt agttaccgag    4080
agcgagagcg ggagcccga gtatcggcag cagtcagcag tgcccctgga cgaagagacc     4140
cacgcaggcg aggacgtggc ggtgttcgcg cgcggcccgc aggcgcacct ggttcacggc    4200
gtgcaggagc agaccttcta agcgcacgtc taggccttcg ccgcctgcct ggagccctac    4260
accgcctgcg acctggcgcc ccccgccggc accaccgacg ccgcgcaccc ggggcggtcc    4320
g                                                                   4321

<210> SEQ ID NO 11
<211> LENGTH: 4665
<212> TYPE: DNA
<213> ORGANISM: Artificial
<220> FEATURE:
<223> OTHER INFORMATION: SA-mAP-3'ABCA4-pA cassette

<400> SEQUENCE: 11
ctaggtggag gccgaaagta caagtttcgc tagggaaccc cagaccctga gtacccagta      60
gactacagcc aaggtgggac caggctggac gggaagaatc tggtgcagga taggctcggc     120
gaacgccagg gtgcccggta cgtgtggaac cgcactgagg tctagcaggc ttccctggac     180
ccgtctgtga ccctactcta gggtctcttt gagcctggag actagaaata cgagatccac     240
cgagactcca cactggaccc ctccctgtag gagtagacag aggctgccct gcgcctgctg     300
agcagacacc cgcgcggctt cttcctcttc gtggagggtg gtcgctacga ccaaggtcat     360
cttgaaagca gggcttaccg ggcactgact gagacgatct agttcgacga cgccttgaga     420
gggcgggcca gctcaccagc gaggaggaca cgctgagcct cgtcactgcc gaccactccc     480
acgtcttctc cttcggaggc taccccctgc gagggaggtc cttcaacggg ctggccgctg     540
gcaaggcccg ggacaggaag gcctacacgg tcctcctata cggaaacggt ccaggcttag     600
```

```
tgctcaagga cggcgcccgg ccggtagtta ccgagagcga gagcgggagc cccgagtatc    660
ggcagcagtc agcagtgccc ctggacgaag agacccacgc aggcgaggac gtggcggtgt    720
tcgcgcgcgg cccgcaggcg cacctggttc acggcgtgca ggagcagacc ttctaagcgc    780
acgtctaggc cttcgccgcc tgcctggagc cctacaccgc ctgcgacctg gcgcccccg     840 ccggcaccac cgacgccgcg cacccggggc ggtccgacta gtaaggagac aatagaaac     900 tgggcttgtc gagacagaga agactcttgc gtttctgata ggcacctatt ggtcttactg    960
acatccactt tgcctttctc tccacaggtg gcatgcagag aaagctgtcg gttgccattg   1020
cctttgtggg agatgccaag gtggtgattc tggacgaacc cacctctggg gtggacccctt  1080 actcgagacg ctcaatctgg gatctgctcc tgaagtatcg ctcaggcaga accatcatca   1140
tgtccactca ccacatggac gaggccgacc tccttgggga ccgcattgcc atcattgccc   1200
agggaaggct ctactgctca ggcaccccac tcttcctgaa gaactgcttt ggcacaggct   1260
tgtacttaac cttggtgcgc aagatgaaaa acatccagag ccaaaggaaa ggcagtgagg   1320
ggacctgcag ctgctcgtct aagggtttct ccaccacgtg tccagcccac gtcgatgacc   1380
taactccaga acaagtcctg gatggggatg taaatgagct gatggatgta gttctccacc   1440
atgttccaga ggcaaagctg gtggagtgca ttggtcaaga acttatcttc cttcttccaa   1500
ataagaactt caagcacaga gcatatgcca gccttttcag agagctggag gagacgctgg   1560
ctgaccttgg tctcagcagt tttggaattt ctgacactcc cctggaagag attttctga   1620 aggtcacgga ggattctgat tcaggacctc tgtttgcggg tggcgctcag cagaaaagag   1680
aaaacgtcaa cccccgacac ccctgcttgg gtcccagaga gaaggctgga cagacacccc   1740
aggactccaa tgtctgctcc ccaggggcgc cggctgctca cccagagggc cagcctcccc   1800
cagagccaga gtgcccaggc ccgcagctca cacggggac acagctggtc ctccagcatg    1860
tgcaggcgct gctggtcaag agattccaac acaccatccg cagccacaag gacttcctgg   1920
cgcagatcgt gctcccggct acctttgtgt ttttggctct gatgctttct attgttatcc   1980
ctcctttggg cgaatacccc gctttgaccc ttcacccctg gatatatggg cagcagtaca   2040
ccttcttcag catggatgaa ccaggcagtg agcagttcac ggtacttgca gacgtcctcc   2100
tgaataagcc aggctttggc aaccgctgcc tgaaggaagg gtggcttccg gagtacccct   2160
gtggcaactc aacaccctgg aagactcctt ctgtgtcccc aaacatcacc cagctgttcc   2220
agaagcagaa atggacacag gtcaacccctt caccatcctg caggtgcagc accagggaga   2280
agctcaccat gctgccagag tgccccgagg gtgccggggg cctcccgccc cccagagaa    2340 cacagcgcag cacggaaatt ctacaagacc tgacggacag gaacatctcc gacttcttgg   2400
taaaaacgta tcctgctctt ataagaagca gcttaaagag caaattctgg gtcaatgaac   2460
agaggtatgg aggaatttcc attggaggaa agctcccagt cgtcccccatc acggggaag    2520 cacttgttgg gttttttaagc gaccttggcc ggatcatgaa tgtgagcggg gccctatca   2580 ctagagaggc ctctaaagaa atacctgatt tccttaaaca tctagaaact gaagacaaca   2640
ttaaggtgtg gtttaataac aaaggctggc atgccctggt cagctttctc aatgtggccc   2700
acaacgccat cttacgggcc agcctgccta aggacaggag ccccgaggag tatggaatca   2760
ccgtcattag ccaacccctg aacctgacca aggagcagct ctcagagatt acagtgctga   2820
ccacttcagt ggatgctgtg gttgccatct gcgtgatttt ctccatgtcc ttcgtcccag   2880
ccagctttgt cctttatttg atccaggagc gggtgaacaa atccaagcac ctccagttta   2940
tcagtggagt gagccccacc acctactggg tgaccaactt cctctgggac atcatgaatt   3000
```

```
attccgtgag tgctgggctg gtggtgggca tcttcatcgg gtttcagaag aaagcctaca    3060
cttctccaga aaaccttcct gcccttgtgg cactgctcct gctgtatgga tgggcggtca    3120
ttcccatgat gtacccagca tccttcctgt tgatgtccc cagcacagcc tatgtggctt     3180
tatcttgtgc taatctgttc atcggcatca acagcagtgc tattaccttc atcttggaat    3240
tatttgagaa taaccggacg ctgctcaggt tcaacgccgt gctgaggaag ctgctcattg    3300
tcttcccca cttctgcctg ggccggggcc tcattgacct tgcactgagc caggctgtga     3360
cagatgtcta tgcccggttt ggtgaggagc actctgcaaa tccgttccac tgggacctga    3420
ttgggaagaa cctgtttgcc atggtggtgg aaggggtggt gtacttcctc ctgacccctgc   3480
tggtccagcg ccacttcttc ctctcccaat ggattgccga gcccactaag gagcccattg    3540
ttgatgaaga tgatgatgtg gctgaagaaa gacaaagaat tattactggt ggaaataaaa    3600
ctgacatctt aaggctacat gaactaacca agatttatcc aggcacctcc agcccagcag    3660
tggacaggct gtgtgtcgga gttcgcccctg gagagtgctt tggcctcctg ggagtgaatg    3720
gtgccggcaa aacaaccaca ttcaagatgc tcactgggga caccacagtg acctcagggg    3780
atgccaccgt agcaggcaag agtattttaa ccaatatttc tgaagtccat caaaatatgg    3840
gctactgtcc tcagtttgat gcaattgatg agctgctcac aggacgagaa catctttacc    3900
tttatgcccg gcttcgaggt gtaccagcag aagaaatcga aaaggttgca aactggagta    3960
ttaagagcct gggcctgact gtctacgccg actgcctggc tggcacgtac agtggggca    4020
acaagcggaa actctccaca gccatcgcac tcattggctg cccaccgctg gtgctgctgg    4080
atgagcccac cacagggatg gaccccagg cacgccgcat gctgtggaac gtcatcgtga     4140
gcatcatcag agaagggagg gctgtggtcc tcacatccca cagcatggaa gaatgtgagg    4200
cactgtgtac ccggctggcc atcatggtaa agggcgcctt tcgatgtatg gcaccattc     4260
agcatctcaa gtccaaattt ggagatggct atatcgtcac aatgaagatc aaatccccga    4320
aggacgacct gcttcctgac ctgaaccctg tggagcagtt cttccagggg aacttcccag    4380
gcagtgtgca gagggagagg cactacaaca tgctccagtt ccaggtctcc tcctcctccc    4440
tggcgaggat cttccagctc ctcctctccc acaaggacag cctgctcatc gaggagtact    4500
cagtcacaca gaccacactg gaccaggtgt tgtaaatttt tgctaaacag cagactgaaa    4560
gtcatgacct ccctctgcac cctcgagctg ctggagccag tcgacaagcc caggactgat    4620
ttaaagatat caataaaata tctttatttt cattacatct gtgtg                   4665
```

<210> SEQ ID NO 12
<211> LENGTH: 5166
<212> TYPE: DNA
<213> ORGANISM: Artificial
<220> FEATURE:
<223> OTHER INFORMATION: AAV-CMV-5'ABCA4-SD-mAP vector

<400> SEQUENCE: 12

```
ctgcgcgctc gctcgctcac tgaggccgcc cgggcaaagc ccgggcgtcg gcgacctttt     60
ggtcgggcgg cctcagtgag cgagcgagcg cgcagagagg gagtggccaa ctccatcact    120
aggggttcct tgtagttaat gattaacccg ccatgctact tatctacgac attgattatt    180
gactagttat taatagtaat caattacggg gtcattagtt catagcccat atatggagtt    240
ccgcgttaca taacttacgg taaatggccc gcctggctga ccgcccaacg acccccgccc    300
attgacgtca ataatgacgt atgttcccat agtaacgcca atagggactt tccattgacg    360
```

```
tcaatgggtg gagtatttac ggtaaactgc ccacttggca gtacatcaag tgtatcatat    420
gccaagtacg cccCctattg acgtcaatga cggtaaatgg cccgcctggc attatgccca    480
gtacatgacc ttatgggact ttcctacttg gcagtacatc tacgtattag tcatcgctat    540
taccatggtg atgcggtttt ggcagtacat caatgggcgt ggatagcggt ttgactcacg    600
gggatttcca agtctccacc ccattgacgt caatgggagt ttgttttggc accaaaatca    660
acgggacttt ccaaaatgtc gtaacaactc cgccccattg acgcaaatgg gcggtaggcg    720
tgtacggtgg gaggtctata taagcagagc tctctggcta actagagaac ccactgctta    780
ctggcttatc gaaattaata cgactcacta taggagacc caagctggct agactcgaga    840
agctttaaag ccaccatggg cttcgtgaga cagatacagc ttttgctctg gaagaactgg    900
accctgcgga aaaggcaaaa gattcgcttt gtggtggaac tcgtgtggcc tttatcttta    960
tttctggtct tgatctggtt aaggaatgcc aacccgctct acagccatca tgaatgccat   1020 tccccaaca aggcgatgcc ctcagcagga atgctgccgt ggctccaggg gatcttctgc   1080
aatgtgaaca atccctgttt tcaaagcccc accccaggag aatctcctgg aattgtgtca   1140
aactataaca actccatctt ggcaagggta tatcgagatt ttcaagaact cctcatgaat   1200
gcaccagaga gccagcacct tggccgtatt tggacagagc tacacatctt gtcccaattc   1260
atggacaccc tccggactca cccggagaga attgcaggaa gaggaatacg aataagggat   1320
atcttgaaag atgaagaaac actgacacta tttctcatta aaaacatcgg cctgtctgac   1380
tcagtggtct accttctgat caactctcaa gtccgtccag agcagttcgc tcatggagtc   1440
ccggacctgg cgctgaagga catcgcctgc agcgaggccc tcctggagcg cttcatcatc   1500
ttcagccaga gacgcggggc aaagacggtg cgctatgccc tgtgctccct ctcccagggc   1560
accctacagt ggatagaaga cactctgtat gccaacgtgg acttcttcaa gctcttccgt   1620
gtgcttccca cactcctaga cagccgttct caaggtatca atctgagatc ttggggagga   1680
atattatctg atatgtcacc aagaattcaa gagtttatcc atcggccgag tatgcaggac   1740
ttgctgtggg tgaccaggcc cctcatgcag aatggtggtc cagagacctt tacaaagctg   1800
atgggcatcc tgtctgacct cctgtgtggc taccccgagg gaggtggctc tcgggtgctc   1860
tccttcaact ggtatgaaga caataactat aaggcctttc tggggattga ctccacaagg   1920
aaggatccta tctattctta tgacagaaga acaacatcct tttgtaatgc attgatccag   1980
agcctggagt caaatccttt aaccaaaatc gcttggaggg cggcaaagcc tttgctgatg   2040
ggaaaaatcc tgtacactcc tgattcacct gcagcacgaa ggatactgaa gaatgccaac   2100
tcaacttttg aagaactgga acacgttagg aagttggtca agcctggga agaagtaggg   2160 ccccagatct ggtacttctt tgacaacagc acacagatga acatgatcag agatacccctg   2220 gggaacccaa cagtaaaaga cttttttgaat aggcagcttg gtgaagaagg tattactgct   2280
gaagccatcc taaacttcct ctacaagggc cctcgggaaa gccaggctga cgacatggcc   2340
aacttcgact ggagggacat atttaacatc actgatcgca ccctccgcct ggtcaatcaa   2400
tacctggagt gcttggtcct ggataagttt gaaagctaca atgatgaaac tcagctcacc   2460
caacgtgccc tctctctact ggaggaaaac atgttctggg ccggagtggt attccctgac   2520
atgtatccct ggaccagctc tctaccaccc cacgtgaagt ataagatccg aatggacata   2580
gacgtggtgg agaaaaccaa taagattaaa gacaggtatt gggattctgg tcccagagct   2640
gatcccgtga agattccg gtacatctgg ggcgggtttg cctatctgca ggacatggtt   2700
gaacagggga tcacaaggag ccaggtgcag gcggaggctc cagttggaat ctacctccag   2760
```

```
cagatgccct acccctgctt cgtggacgat tctttcatga tcatcctgaa ccgctgtttc    2820
cctatcttca tggtgctggc atggatctac tctgtctcca tgactgtgaa gagcatcgtc    2880
ttggagaagg agttgcgact gaaggagacc ttgaaaaatc agggtgtctc caatgcagtg    2940
atttggtgta cctggttcct ggacagcttc tccatcatgt cgatgagcat cttcctcctg    3000
acgatattca tcatgcatgg aagaatccta cattacagcg acccattcat cctcttcctg    3060
ttcttgttgg ctttctccac tgccaccatc atgctgtgct ttctgctcag caccttcttc    3120
tccaaggcca gtctggcagc agcctgtagt ggtgtcatct atttcaccct ctacctgcca    3180
cacatcctgt gcttcgcctg gcaggaccgc atgaccgctg agctgaagaa ggctgtgagc    3240
ttactgtctc cggtggcatt tggatttggc actgagtacc tggttcgctt tgaagagcaa    3300
ggcctggggc tgcagtggag caacatcggg aacagtccca cggaagggga cgaattcagc    3360
ttcctgctgt ccatgcagat gatgctcctt gatgctgctg tctatggctt actcgcttgg    3420
taccttgatc aggtgtttcc aggagactat ggaaccccac ttccttggta ctttcttcta    3480
caagagtcgt attggcttgg cggtgaaggg tgttcaacca gagaagaaag agccctggaa    3540
aagaccgagc ccctaacaga ggaaacggag gatccagagc acccgaagg aatacacgac     3600 tccttctttg aacgtgagca tccagggtgg gttcctgggg tatgcgtgaa gaatctggta    3660 aagattttg agccctgtgg ccggccagct gtggaccgtc tgaacatcac cttctacgag     3720
aaccagatca ccgcattcct gggccacaat ggagctggga aaaccaccac cttgtccatc    3780
ctgacgggtc tgttgccacc aacctctggg actgtgctcg ttgggggaag gacattgaa     3840 accagcctgg atgcagtccg gcagagcctt ggcatgtgtc cacagcacaa catcctgttc    3900
caccacctca cggtggctga gcacatgctg ttctatgccc agctgaaagg aaagtcccag    3960
gaggaggccc agctggagat ggaagccatg ttggaggaca caggcctcca ccacaagcgg    4020
aatgaagagg ctcaggacct atcaggtaag tatcaaggtt acaagacagg tttccgcggc    4080
ctaggtggag gccgaaagta caagtttcgc tagggaaccc cagaccctga gtacccagta    4140
gactacagcc aaggtgggac caggctggac gggaagaatc tggtgcagga taggctcggc    4200
gaacgccagg gtgcccggta cgtgtggaac cgcactgagg tctagcaggc ttccctggac    4260
ccgtctgtga ccctactcta gggtctcttt gagcctggag actagaaata cgagatccac    4320
cgagactcca cactggaccc ctccctgtag gagtagacag aggctgccct cgcctgctg     4380 agcagacacc cgcgcggctt cttcctcttc gtggagggtg gtcgctacga ccaaggtcat    4440
cttgaaagca gggcttaccg ggcactgact gagacgatct agttcgacga cgccttgaga    4500
gggcgggcca gctcaccagc gaggaggaca cgctgagcct cgtcactgcc gaccactccc    4560
acgtcttctc cttcggaggc tacccctgc gagggaggtc cttcaacggg ctggccgctg     4620
gcaaggcccg ggacaggaag gcctacacgg tcctcctata cggaaacggt ccaggcttag    4680
tgctcaagga cggcgcccgg ccggtagtta ccgagagcga gagcgggagc ccgagtatc     4740 ggcagcagtc agcagtgccc ctggacgaag agacccacgc aggcgaggac gtggcggtgt    4800
tcgcgcgcgg cccgcaggcg cacctggttc acggcgtgca ggagcagacc ttctaagcgc    4860
acgtctaggc cttcgccgcc tgcctggagc cctacaccgc ctgcgacctg gcgcccccg     4920 ccggcaccac cgacgccgcg cacccggggc ggtccgacta gcggatccat cgataaggat    4980
cttcctagag catggctacg tagataagta gcatggcggg ttaatcatta actcaagga     5040 accctagtg atggagttgg ccactccctc tctgcgcgct cgctcgctca ctgaggccgg     5100
```

```
gcgaccaaag gtcgcccgac gcccgggctt tgcccgggcg gcctcagtga gcgagcgagc    5160
gcgcag                                                                5166

<210> SEQ ID NO 13
<211> LENGTH: 4744
<212> TYPE: DNA
<213> ORGANISM: Artificial
<220> FEATURE:
<223> OTHER INFORMATION: AAV-RK-5'ABCA4-SD-mAP vector

<400> SEQUENCE: 13
ctgcgcgctc gctcgctcac tgaggccgcc cgggcaaagc ccgggcgtcg ggcgaccttt      60
ggtcgggcgg cctcagtgag cgagcgagcg cgcagagagg gagtggccaa ctccatcact     120
aggggttcct tgtagttaat gattaacccg ccatgctact tatctacgac attgattatt     180
gactagtccg gatccaagct cagatctcga gttgggcccc agaagcctgg tggttgtttg     240
tccttctcag gggaaaagtg aggcggcccc ttggaggaag gggccgggca gaatgatcta     300
atcggattcc aagcagctca ggggattgtc ttttctagc accttcttgc cactcctaag      360
cgtcctccgt gaccccggct gggatttagc ctggtgctgt gtcagcccg ggtcgacaag      420 ctttaaagcc accatgggct tcgtgagaca gatacagctt ttgctctgga gaactggac     480 cctgcggaaa aggcaaaaga ttcgctttgt ggtggaactc gtgtggcctt tatctttatt     540
tctggtcttg atctggttaa ggaatgccaa cccgctctac agccatcatg aatgccattt     600
ccccaacaag gcgatgccct cagcaggaat gctgccgtgg ctccagggga tcttctgcaa     660
tgtgaacaat ccctgttttc aaagccccac cccaggagaa tctcctggaa ttgtgtcaaa     720
ctataacaac tccatcttgg caagggtata tcgagatttt caagaactcc tcatgaatgc     780
accagagagc cagcaccttg gccgtatttg gacagagcta cacatcttgt cccaattcat     840
ggacacccct cggactcacc cggagagaat gcaggaaga ggaatacgaa taagggatat      900
cttgaaagat gaagaaacac tgacactatt tctcattaaa aacatcggcc tgtctgactc     960
agtggtctac cttctgatca actctcaagt ccgtccagag cagttcgctc atggagtccc    1020
ggacctggcg ctgaaggaca tcgcctgcag cgaggccctc ctggagcgct tcatcatctt    1080
cagccagaga cgcggggcaa agacggtgcg ctatgccctg tgctccctct cccagggcac    1140
cctacagtgg atagaagaca ctctgtatgc caacgtggac ttcttcaagc tcttccgtgt    1200
gcttcccaca ctcctagaca gccgttctca aggtatcaat ctgagatctt ggggaggaat    1260
attatctgat atgtcaccaa gaattcaaga gtttatccat cggccgagta tgcaggactt    1320
gctgtgggtg accaggcccc tcatgcagaa tggtggtcca gagacccttta caaagctgat    1380 gggcatcctg tctgacctcc tgtgtggcta ccccgaggga ggtggctctc gggtgctctc    1440
cttcaactgg tatgaagaca ataactataa ggcctttctg gggattgact ccacaaggaa    1500
ggatcctatc tattcttatg acagaagaac aacatccttt tgtaatgcat tgatccagag    1560
cctggagtca atcctttaa ccaaaatcgc ttggagggcg gcaaagcctt tgctgatggg    1620
aaaaatcctg tacactcctg attcacctgc agcacgaagg atactgaaga atgccaactc    1680
aacttttgaa gaactggaac acgttaggaa gttggtcaaa gctgggaag aagtagggcc    1740 ccagatctgg tacttctttg acaacagcac acagatgaac atgatcagag ataccctggg    1800
gaacccaaca gtaaaagact ttttgaatag gcagcttggt gaagaaggta ttactgctga    1860
agccatccta aacttcctct acaagggccc tcgggaaagc caggctgacg acatggccaa    1920
cttcgactgg agggacatat ttaacatcac tgatcgcacc ctccgcctgg tcaatcaata    1980
```

```
cctggagtgc ttggtcctgg ataagtttga aagctacaat gatgaaactc agctcaccca    2040
acgtgccctc tctctactgg aggaaaacat gttctgggcc ggagtggtat tccctgacat    2100
gtatccctgg accagctctc taccacccca cgtgaagtat aagatccgaa tggacataga    2160
cgtggtggag aaaaccaata agattaaaga caggtattgg gattctggtc ccagagctga    2220
tcccgtggaa gatttccggt acatctgggg cgggtttgcc tatctgcagg acatggttga    2280 acagggatc acaaggagcc aggtgcaggc ggaggctcca gttggaatct acctccagca    2340
gatgccctac ccctgcttcg tggacgattc tttcatgatc atcctgaacc gctgtttccc    2400
tatcttcatg gtgctggcat ggatctactc tgtctccatg actgtgaaga gcatcgtctt    2460
ggagaaggag ttgcgactga aggagacctt gaaaaatcag ggtgtctcca atgcagtgat    2520
ttggtgtacc tggttcctgg acagcttctc catcatgtcg atgagcatct tcctcctgac    2580
gatattcatc atgcatggaa gaatcctaca ttacagcgac ccattcatcc tcttcctgtt    2640
cttgttggct ttctccactg ccaccatcat gctgtgcttt ctgctcagca ccttcttctc    2700
caaggccagt ctggcagcag cctgtagtgg tgtcatctat ttcaccctct acctgccaca    2760
catcctgtgc ttcgcctggc aggaccgcat gaccgctgag ctgaagaagg ctgtgagctt    2820
actgtctccg gtggcatttg gatttggcac tgagtacctg gttcgctttg aagagcaagg    2880
cctggggctg cagtggagca acatcgggaa cagtcccacg gaaggggacg aattcagctt    2940
cctgctgtcc atgcagatga tgctccttga tgctgctgtc tatggcttac tcgcttggta    3000
ccttgatcag gtgtttccag agactatgg aaccccactt ccttggtact ttcttctaca    3060
agagtcgtat tggcttggcg gtgaagggtg ttcaaccaga gaagaaagag ccctggaaaa    3120
gaccgagccc ctaacagagg aaacggagga tccagagcac ccagaaggaa tacacgactc    3180
cttctttgaa cgtgagcatc agggtgggt tcctggggta tgcgtgaaga atctggtaaa    3240 gattttttgag ccctgtggcc ggccagctgt ggaccgtctg aacatcaccct tctacgagaa    3300 ccagatcacc gcattcctgg ccacaatgg agctgggaaa accaccacct tgtccatcct    3360
gacgggtctg ttgccaccaa cctctgggac tgtgctcgtt gggggaaggg acattgaaac    3420
cagcctggat gcagtccggc agagccttgg catgtgtcca cagcacaaca tcctgttcca    3480
ccacctcacg gtggctgagc acatgctgtt ctatgcccag ctgaaaggaa agtcccagga    3540
ggaggcccag ctggagatgg aagccatgtt ggaggacaca ggcctccacc acaagcggaa    3600
tgaagaggct caggacctat caggtaagta tcaaggttac aagacaggtt ccgcggcct    3660 aggtggaggc cgaaagtaca agtttcgcta gggaacccca gaccctgagt cccagtaga    3720 ctacagccaa ggtgggacca ggctggacgg gaagaatctg gtgcaggata ggctcggcga    3780
acgccagggt gcccggtacg tgtggaaccg cactgaggtc tagcaggctt ccctggaccc    3840
gtctgtgacc ctactctagg gtctctttga gcctggagac tagaaatacg agatccaccg    3900
agactccaca ctggacccct ccctgtagga gtagacagag gctgccctgc gcctgctgag    3960
cagacacccg cgcggcttct tcctcttcgt ggagggtggt cgctacgacc aaggtcatct    4020
tgaaagcagg gcttaccggg cactgactga gacgatctag ttcgacgacg ccttgagagg    4080
gcgggccagc tcaccagcga ggaggacacg ctgagcctcg tcactgccga ccactcccac    4140
gtcttctcct tcggaggcta ccccctgcga gggaggtcct tcaacgggct ggccgctggc    4200
aaggcccggg acaggaaggc ctacacggtc tccctatacg gaaacggtcc aggcttagtg    4260
ctcaaggacg gcgcccggcc ggtagttacc gagagcgaga gcgggagccc cgagtatcgg    4320
```

```
cagcagtcag cagtgcccct ggacgaagag acccacgcag gcgaggacgt ggcggtgttc    4380
gcgcgcggcc cgcaggcgca cctggttcac ggcgtgcagg agcagacctt ctaagcgcac    4440
gtctaggcct tcgccgcctg cctggagccc tacaccgcct gcgacctggc gccccccgcc    4500
ggcaccaccg acgccgcgca cccggggcgg tccgactagc ggatccatcg ataaggatct    4560
tcctagagca tggctacgta gataagtagc atggcgggtt aatcattaac tacaaggaac    4620
ccctagtgat ggagttggcc actccctctc tgcgcgctcg ctcgctcact gaggccgggc    4680
gaccaaaggt cgcccgacgc ccgggctttg cccggcggg ctcagtgagc gagcgagcgc    4740
gcag                                                                 4744
```

<210> SEQ ID NO 14
<211> LENGTH: 5024
<212> TYPE: DNA
<213> ORGANISM: Artificial
<220> FEATURE:
<223> OTHER INFORMATION: AAV-SA-mAP-3'ABCA4-pA vector

<400> SEQUENCE: 14

```
ctgcgcgctc gctcgctcac tgaggccgcc cgggcaaagc ccgggcgtcg ggcgaccttt      60
ggtcgggcgg cctcagtgag cgagcgagcg cgcagagagg gagtggccaa ctccatcact    120
aggggttcct tgtagttaat gattaacccg ccatgctact tatctacgac attgattatt    180
gactaggtgg aggccgaaag tacaagtttc gctaggggaac cccagaccct gagtacccag    240
tagactacag ccaaggtggg accaggctgg acgggaagaa tctggtgcag gataggctcg    300
gcgaacgcca gggtgcccgg tacgtgtgga accgcactga ggtctagcag gcttccctgg    360
acccgtctgt gaccctactc tagggtctct ttgagcctgg agactagaaa tacgagatcc    420
accgagactc cacactggac ccctcccgt aggagtagac agaggctgcc ctgcgcctgc    480
tgagcagaca cccgcgcggc ttcttcctct tcgtggaggg tggtcgctac gaccaaggtc    540
atcttgaaag cagggcttac cgggcactga ctgagacgat ctagttcgac gacgccttga    600
gagggcgggc cagctcacca gcgaggagga cacgctgagc ctcgtcactg ccgaccactc    660
ccacgtcttc tccttcggag gctaccccct gcgagggagg tccttcaacg ggctggccgc    720
tggcaaggcc cgggacagga aggcctacac ggtcctccta tacggaaacg gtccaggctt    780
agtgctcaag gacggcgccc ggccggtagt taccgagagc gagagcggga gccccgagta    840
tcggcagcag tcagcagtgc ccctggacga agagacccac gcaggcgagg acgtggcggt    900
gttcgcgcgc ggcccgcagg cgcacctggt tcacggcgtg caggagcaga ccttctaagc    960
gcacgtctag gccttcgccg cctgcctgga gccctacacc gcctgcgacc tggcgccccc    1020
cgccggcacc accgacgccg cgcacccggg cggtccgac tagtaaggag accaatagaa    1080
actgggcttg tcgagacaga gaagactctt gcgtttctga taggcaccta ttggtcttac    1140
tgacatccac tttgcctttc tctccacagg tggcatgcag agaaagctgt cggttgccat    1200
tgcctttgtg ggagatgcca aggtggtgat tctggacgaa cccaccctg gggtggaccc    1260 ttactcgaga cgctcaatct gggatctgct cctgaagtat cgctcaggca gaaccatcat    1320
catgtccact caccacatgg acgaggccga cctccttggg gaccgcattg ccatcattgc    1380
ccagggaagg ctctactgct caggcaccc actcttcctg aagaactgct ttggcacagg    1440
cttgtactta accttggtgc gcaagatgaa aaacatccag agccaaagga aaggcagtga    1500
ggggacctgc agctgctcgt ctaagggttt ctccaccacg tgtccagccc acgtcgatga    1560
cctaactcca gaacaagtcc tggatgggga tgtaaatgag ctgatggatg tagttctcca    1620
```

```
ccatgttcca gaggcaaagc tggtggagtg cattggtcaa gaacttatct tccttcttcc    1680
aaataagaac ttcaagcaca gagcatatgc cagccttttc agagagctgg aggagacgct    1740
ggctgacctt ggtctcagca gttttggaat ttctgacact cccctggaag agatttttct    1800
gaaggtcacg gaggattctg attcaggacc tctgtttgcg ggtggcgctc agcagaaaag    1860
agaaaacgtc aaccccgac accctgctt gggtcccaga gagaaggctg acagacacc      1920 ccaggactcc aatgtctgct ccccagggc gccggctgct cacccagagg gccagcctcc    1980
cccagagcca gagtgcccag gcccgcagct caacacgggg acacagctgg tcctccagca   2040
tgtgcaggcg ctgctggtca agagattcca acacaccatc cgcagccaca aggacttcct   2100
ggcgcagatc gtgctcccgg ctacctttgt gttttggct ctgatgcttt ctattgttat    2160
ccctcctttt ggcgaatacc ccgctttgac ccttcacccc tggatatatg gcagcagta    2220 caccttcttc agcatggatg aaccaggcag tgagcagttc acggtacttg cagacgtcct   2280
cctgaataag ccaggctttg caaccgctg cctgaaggaa gggtggcttc cggagtaccc    2340
ctgtggcaac tcaacaccct ggaagactcc ttctgtgtcc ccaaacatca cccagctgtt   2400
ccagaagcag aaatggacac aggtcaaccc ttcaccatcc tgcaggtgca gcaccaggga   2460
gaagctcacc atgctgccag agtgccccga gggtgccggg ggcctcccgc cccccagag    2520 aacacagcgc agcacggaaa ttctacaaga cctgacggac aggaacatct ccgacttctt   2580
ggtaaaaacg tatcctgctc ttataagaag cagcttaaag agcaaattct gggtcaatga   2640
acagaggtat ggaggaattt ccattggagg aaagctccca gtcgtcccca tcacgggga    2700 agcacttgtt gggtttttaa gcgaccttgg ccggatcatg aatgtgagcg gggccctat    2760 cactagagag gcctctaaag aaatacctga tttccttaaa catctagaaa ctgaagacaa   2820
cattaaggtg tggtttaata caaaggctg gcatgccctg gtcagctttc tcaatgtggc   2880
ccacaacgcc atcttacggg ccagcctgcc taaggacagg agcccgagg agtatggaat    2940 caccgtcatt agccaacccc tgaacctgac caaggagcag ctctcagaga ttacagtgct   3000
gaccacttca gtggatgctg tggttgccat ctgcgtgatt ttctccatgt ccttcgtccc   3060
agccagcttt gtcctttatt tgatccagga gcgggtgaac aaatccaagc acctccagtt   3120
tatcagtgga gtgagcccca ccacctactg ggtgaccaac ttcctctggg acatcatgaa   3180
ttattccgtg agtgctgggc tggtggtggg catcttcatc gggtttcaga gaaagcctat   3240
cacttctcca gaaaaccttc ctgcccttgt ggcactgctc ctgctgtatg atgggcggt    3300 cattcccatg atgtacccag catccttcct gtttgatgtc cccagcacag cctatgtggc   3360
tttatcttgt gctaatctgt tcatcggcat caacagcagt gctattacct tcatcttgga   3420
attatttgag aataaccgga cgctgctcag gttcaacgcc gtgctgagga agctgctcat   3480
tgtcttcccc cacttctgcc tgggccgggg cctcattgac cttgcactga gccaggctgt   3540
gacagatgtc tatgcccggt ttggtgagga gcactctgca aatccgttcc actgggacct   3600
gattgggaag aacctgtttg ccatggtggt ggaaggggtg gtgtacttcc tcctgaccct   3660
gctggtccag cgccacttct tcctctccca atggattgcc gagcccacta aggagcccat   3720
tgttgatgaa gatgatgatg tggctgaaga agacaaaga attattactg gtggaaataa    3780
aactgacatc ttaaggctac atgaactaac caagatttat ccaggcacct ccagcccagc   3840
agtggacagc tgtgtgtcg gagttcgccc tggagagtgc tttggcctcc tgggagtgaa    3900
tggtgccggc aaaacaacca cattcaagat gctcactggg gacaccacag tgacctcagg   3960
```

```
ggatgccacc gtagcaggca agagtatttt aaccaatatt tctgaagtcc atcaaaatat    4020
gggctactgt cctcagtttg atgcaattga tgagctgctc acaggacgag aacatcttta    4080
cctttatgcc cggcttcgag gtgtaccagc agaagaaatc gaaaaggttg caaactggag    4140
tattaagagc ctgggcctga ctgtctacgc cgactgcctg gctggcacgt acagtgggg     4200 caacaagcgg aaactctcca cagccatcgc actcattggc tgcccaccgc tggtgctgct    4260
ggatgagccc accacaggga tggacccca ggcacgccgc atgctgtgga acgtcatcgt     4320
gagcatcatc agagaaggga gggctgtggt cctcacatcc cacagcatgg aagaatgtga    4380
ggcactgtgt acccggctgg ccatcatggt aaagggcgcc tttcgatgta tgggcaccat    4440
tcagcatctc aagtccaaat tggagatgg ctatatcgtc acaatgaaga tcaaatcccc     4500
gaaggacgac ctgcttcctg acctgaaccc tgtggagcag ttcttccagg ggaacttccc    4560
aggcagtgtg cagagggaga ggcactacaa catgctccag ttccaggtct cctcctcctc    4620
cctggcgagg atcttccagc tcctcctctc ccacaaggac agcctgctca tcgaggagta    4680
ctcagtcaca cagaccacac tggaccaggt gtttgtaaat tttgctaaac agcagactga    4740
aagtcatgac ctccctctgc accctcgagc tgctggagcc agtcgacaag cccaggactg    4800
atttaaagat atcaataaaa tatctttatt ttcattacat ctgtgtgaat cgattacgta    4860
gataagtagc atggcgggtt aatcattaac tacaaggaac ccctagtgat ggagttggcc    4920
actccctctc tgcgcgctcg ctcgctcact gaggccgggc gaccaaaggt cgcccgacgc    4980
ccgggctttg cccgggcggc ctcagtgagc gagcgagcgc gcag                     5024
```